United States Patent
Iwata et al.

(10) Patent No.: US 8,389,952 B2
(45) Date of Patent: Mar. 5, 2013

(54) PARTICLE BEAM IRRADIATION APPARATUS AND PARTICLE BEAM THERAPY SYSTEM

(75) Inventors: Takaaki Iwata, Chiyoda-ku (JP); Yuehu Pu, Chiyoda-ku (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 0 days.

(21) Appl. No.: 13/322,201

(22) PCT Filed: Apr. 13, 2011

(86) PCT No.: PCT/JP2011/059169
§ 371 (c)(1),
(2), (4) Date: Nov. 23, 2011

(87) PCT Pub. No.: WO2012/008190
PCT Pub. Date: Jan. 19, 2012

(65) Prior Publication Data
US 2012/0132826 A1 May 31, 2012

(30) Foreign Application Priority Data
Jul. 14, 2010 (WO) .................. PCT/JP2010/061876

(51) Int. Cl.
*H01J 3/26* (2006.01)
*H01J 1/50* (2006.01)
*A61N 5/00* (2006.01)
(52) U.S. Cl. ....... 250/396 ML; 250/396 R; 250/493.33; 250/492.3
(58) Field of Classification Search ........... 250/396 ML, 250/396 R, 397, 398, 492.1, 492.22, 492.3
See application file for complete search history.

(56) References Cited

U.S. PATENT DOCUMENTS
(Continued)

FOREIGN PATENT DOCUMENTS
JP 8-257148 A 10/1996
JP 10-300899 A 11/1998
(Continued)

OTHER PUBLICATIONS
International Search Report (PCT/ISA/210) issued on Jun. 28, 2011, by Japanese Patent Office as the International Searching Authority for International Application No. PCT/JP2011/059169.
(Continued)

*Primary Examiner* — Bernard E Souw
(74) *Attorney, Agent, or Firm* — Buchanan Ingersoll & Rooney

(57) ABSTRACT

There is provided a particle beam irradiation apparatus in which two or more pairs of scanning electromagnets are utilized so that scanning of a charged particle beam can be performed with a high accuracy and with a high flexibility in the speed, from a low speed to a high speed. In a particle beam irradiation apparatus that scans an incident charged particle beam on X-direction and Y-direction (two-direction) desired orbits perpendicular to the travelling direction of the charged particle beam and irradiates the charged particle beam onto an irradiation subject, there are provided two or more pairs of scanning electromagnets that scan a charged particle beam in the two directions; the desired orbit is given by time-series desired orbit data in which desired irradiation positions corresponding to time are determined; and command values for respective scanning electromagnets in the two or more pairs of scanning electromagnets are generated based on plural pieces of data obtained by frequency-separating the time-series desired orbit data.

10 Claims, 21 Drawing Sheets

U.S. PATENT DOCUMENTS

2002/0033456 A1 3/2002 Tachikawa et al.
2010/0213384 A1 8/2010 Furukawa et al.
2011/0240875 A1* 10/2011 Iwata .......................... 250/397

FOREIGN PATENT DOCUMENTS

| JP | 2002-022900 A | 1/2002 |
| JP | 2006-346120 A | 12/2006 |
| JP | 2008-154627 A | 7/2008 |

OTHER PUBLICATIONS

Written Opinion (PCT/ISA/237) issued on Jun. 28, 2011, by Japanese Patent Office as the International Searching Authority for International Application No. PCT/JP2011/059169.

* cited by examiner

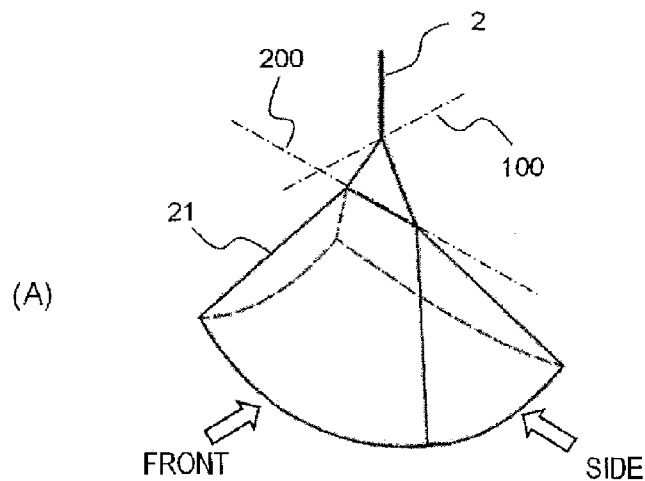
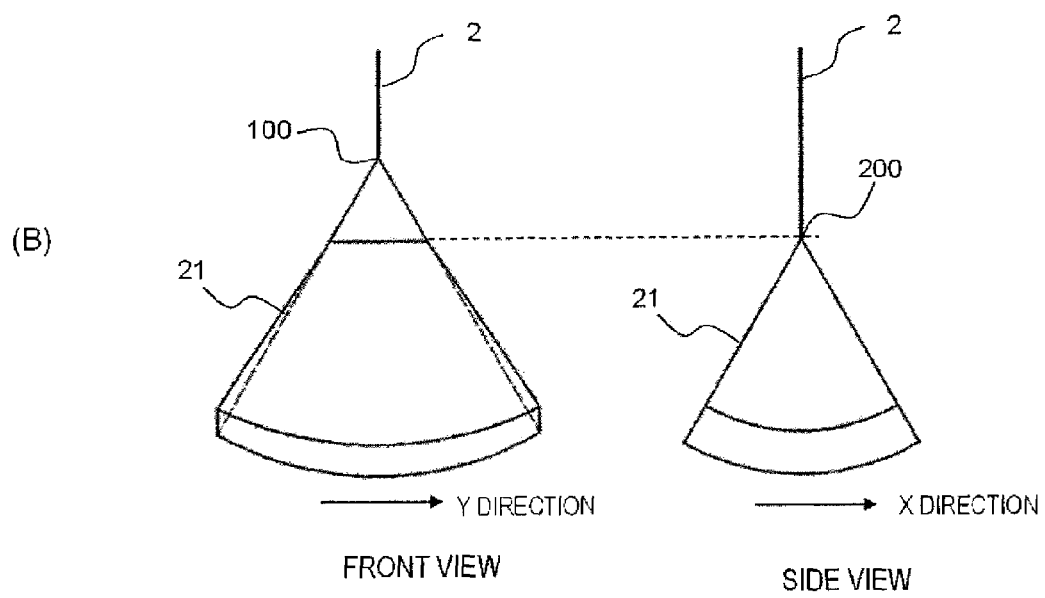
FIG. 3

Table 1

| | | |
|---|---|---|
| INPUT | INPUT1 | COMMAND VALUE I1x FOR X-DIRECTION SCANNING ELECTROMAGNET 52 |
| | INPUT2 | COMMAND VALUE I1y FOR Y-DIRECTION SCANNING ELECTROMAGNET 51 |
| | INPUT3 | COMMAND VALUE I2x FOR X-DIRECTION SCANNING ELECTROMAGNET 62 |
| | INPUT4 | COMMAND VALUE I2y FOR Y-DIRECTION SCANNING ELECTROMAGNET 61 |
| OUTPUT | OUTPUT1 | X-DIRECTION COMPONENT x1 OF BEAM TRAVEL AMOUNT OP1 CAUSED BY FIRST SCANNING ELECTROMAGNET 5 |
| | OUTPUT2 | Y-DIRECTION COMPONENT y1 OF BEAM TRAVEL AMOUNT OP1 CAUSED BY FIRST SCANNING ELECTROMAGNET 5 |
| | OUTPUT3 | X-DIRECTION COMPONENT x OF EVENTUAL BEAM TRAVEL AMOUNT OP2 |
| | OUTPUT4 | Y-DIRECTION COMPONENT y OF EVENTUAL BEAM TRAVEL AMOUNT OP2 |

FIG. 14

Table 2

| | | |
|---|---|---|
| INPUT | INPUT1 | COMMAND VALUE I1x FOR X-DIRECTION SCANNING ELECTROMAGNET 52 |
| | INPUT2 | COMMAND VALUE I1y FOR Y-DIRECTION SCANNING ELECTROMAGNET 51 |
| | INPUT3 | COMMAND VALUE I2x FOR X-DIRECTION SCANNING ELECTROMAGNET 62 |
| | INPUT4 | COMMAND VALUE I2y FOR Y-DIRECTION SCANNING ELECTROMAGNET 61 |
| OUTPUT | OUTPUT1 | X-DIRECTION COMPONENT x1 OF BEAM TRAVEL AMOUNT OP1 CAUSED BY FIRST SCANNING ELECTROMAGNET 5 |
| | OUTPUT2 | Y-DIRECTION COMPONENT y1 OF BEAM TRAVEL AMOUNT OP1 CAUSED BY FIRST SCANNING ELECTROMAGNET 5 |
| | OUTPUT3 | X-DIRECTION COMPONENT x2 OF BEAM TRAVEL AMOUNT P1P2 CAUSED BY SECOND SCANNING ELECTROMAGNET 6 |
| | OUTPUT4 | Y-DIRECTION COMPONENT y2 OF BEAM TRAVEL AMOUNT P1P2 CAUSED BY SECOND SCANNING ELECTROMAGNET 6 |

FIG. 15

Table 3

| | |
|---|---|
| $x_1$ | X-DIRECTION COMPONENT OF DESIRED BEAM TRAVEL AMOUNT CAUSED BY FIRST SCANNING ELECTROMAGNET |
| $y_1$ | Y-DIRECTION COMPONENT OF DESIRED BEAM TRAVEL AMOUNT CAUSED BY FIRST SCANNING ELECTROMAGNET |
| $\hat{I}_{1x}$ | ESTIMATED COMMAND VALUE FOR X-DIRECTION SCANNING ELECTROMAGNET TO ACHIEVE DESIRED BEAM TRAVEL AMOUNT CAUSED BY FIRST SCANNING ELECTROMAGNET |
| $\hat{I}_{1y}$ | ESTIMATED COMMAND VALUE FOR Y-DIRECTION SCANNING ELECTROMAGNET TO ACHIEVE DESIRED BEAM TRAVEL AMOUNT CAUSED BY FIRST SCANNING ELECTROMAGNET |
| $a_{mn}$ | UNKNOWN PARAMETER OF INVERSE-MAP FORMULA MODEL FOR OBTAINING $\hat{I}_{1x}$ (COEFFICIENT OF POLYNOMINAL (2)) |
| $b_{mn}$ | UNKNOWN PARAMETER OF INVERSE-MAP FORMULA MODEL FOR OBTAINING $\hat{I}_{1y}$ (COEFFICIENT OF POLYNOMINAL (3)) |

FIG. 16

Table 4

| | |
|---|---|
| $x_1$ | X-DIRECTION COMPONENT OF DESIRED BEAM TRAVEL AMOUNT CAUSED BY FIRST SCANNING ELECTROMAGNET |
| $y_1$ | Y-DIRECTION COMPONENT OF DESIRED BEAM TRAVEL AMOUNT CAUSED BY FIRST SCANNING ELECTROMAGNET |
| $x$ | X-DIRECTION COMPONENT OF EVENTUAL DESIRED BEAM TRAVEL AMOUNT |
| $y$ | Y-DIRECTION COMPONENT OF EVENTUAL DESIRED BEAM TRAVEL AMOUNT |
| $\hat{i}_{2x}$ | ESTIMATED COMMAND VALUE FOR X-DIRECTION SCANNING ELECTROMAGNET TO ACHIEVE DESIRED BEAM TRAVEL AMOUNT CAUSED BY SECOND SCANNING ELECTROMAGNET |
| $\hat{i}_{2y}$ | ESTIMATED COMMAND VALUE FOR Y-DIRECTION SCANNING ELECTROMAGNET TO ACHIEVE DESIRED BEAM TRAVEL AMOUNT CAUSED BY SECOND SCANNING ELECTROMAGNET |
| $c_{mnpq}$ | UNKNOWN PARAMETER OF INVERSE-MAP FORMULA MODEL FOR OBTAINING $\hat{i}_{2x}$ (COEFFICIENT OF POLYNOMINAL (4)) |
| $d_{mnpq}$ | UNKNOWN PARAMETER OF INVERSE-MAP FORMULA MODEL FOR OBTAINING $\hat{i}_{2y}$ (COEFFICIENT OF POLYNOMINAL (5)) |

FIG. 19

Table 5

| | |
|---|---|
| $x_1$ | X-DIRECTION COMPONENT OF DESIRED BEAM TRAVEL AMOUNT CAUSED BY FIRST SCANNING ELECTROMAGNET |
| $y_1$ | Y-DIRECTION COMPONENT OF DESIRED BEAM TRAVEL AMOUNT CAUSED BY FIRST SCANNING ELECTROMAGNET |
| $x_2$ | X-DIRECTION COMPONENT OF DESIRED BEAM TRAVEL AMOUNT CAUSED BY SECOND SCANNING ELECTROMAGNET |
| $y_2$ | Y-DIRECTION COMPONENT OF DESIRED BEAM TRAVEL AMOUNT CAUSED BY SECOND SCANNING ELECTROMAGNET |
| $\hat{I}_{2x}$ | ESTIMATED COMMAND VALUE FOR X-DIRECTION SCANNING ELECTROMAGNET TO ACHIEVE DESIRED BEAM TRAVEL AMOUNT CAUSED BY SECOND SCANNING ELECTROMAGNET |
| $\hat{I}_{2y}$ | ESTIMATED COMMAND VALUE FOR Y-DIRECTION SCANNING ELECTROMAGNET TO ACHIEVE DESIRED BEAM TRAVEL AMOUNT CAUSED BY SECOND SCANNING ELECTROMAGNET |
| $e_{mnpq}$ | UNKNOWN PARAMETER OF INVERSE-MAP FORMULA MODEL FOR OBTAINING $\hat{I}_{2x}$ (COEFFICIENT OF POLYNOMINAL (6)) |
| $f_{mnpq}$ | UNKNOWN PARAMETER OF INVERSE-MAP FORMULA MODEL FOR OBTAINING $\hat{I}_{2y}$ (COEFFICIENT OF POLYNOMINAL (7)) |

FIG. 20

PARTICLE BEAM IRRADIATION APPARATUS AND PARTICLE BEAM THERAPY SYSTEM

TECHNICAL FIELD

The present invention relates to a particle beam irradiation apparatus, for irradiating a charged particle beam in accordance with the three-dimensional shape of a diseased site, which is included in a particle beam therapy system that performs therapy by irradiating a charged particle beam onto a diseased site such as a tumor.

BACKGROUND ART

In a treatment method based on a particle beam, there is utilized a high-energy charged particle beam such as a proton beam or a carbon beam accelerated up to 70% of the light velocity. These high-energy charged particle beams have the following features when irradiated into a body. Firstly, almost all of irradiated charged particles stop at a position of the depth proportional to the charged particle energy raised to the $1.7^{th}$ power. Secondly, the density (referred to as a dose) of energy, which is given to the path through which an irradiated charged particle passes until it stops in a body, becomes maximum at a position where the charged particle stops. A distinctive deep dose distribution curve formed along a path through which a charged particle beam passes is referred to as a Bragg curve. The position where the dose value becomes maximum is referred to as a Bragg peak.

A three-dimensional particle beam irradiation system is contrived in such a way that, while it scans the Bragg peak position in accordance with the three-dimensional shape of a tumor and adjusts the peak dose at each scanning position, a predetermined three-dimensional dose distribution is formed in a tumor region, which is a target preliminarily determined by an imaging diagnosis. The scanning of a charged particle beam stops includes scanning in transverse directions (X and Y directions) that are approximately perpendicular to the irradiation direction of the charged particle beam and scanning in a depth direction (Z direction) that is the irradiation direction of the charged particle beam. In the transverse-direction scanning, there exist a method of moving a patient with respect to a charged particle beam and a method of moving the position of a charged particle beam with an electromagnet or the like; in general, the method utilizing an electromagnet is adopted. Scanning in the depth direction is performed only by changing the energy of a charged particle. As the method of changing energy, there exist a method of changing the energy of a charged particle by means of an accelerator and a method of inserting an energy attenuator into a path through which a charged particle beam passes and changing the attenuation amount of the attenuator.

The method of moving (referred to also as scanning) the position of a charged particle beam with an electromagnet is disclosed, for example, in Patent Document. As illustrated in FIG. 2 of Patent Document 1, in a particle beam irradiation system of a conventional particle beam therapy system, as a means for moving the position of a beam spot, a scanning magnet (scanning electromagnet) that deflects a charged particle beam to the X-Y direction, which is a direction perpendicular to the traveling direction of a beam (the Z direction), is utilized.

A particle beam irradiation apparatus disclosed in Patent Document 2 is configured in such a way that two or more scanning electromagnets which are separately dedicated to the X direction and the Y direction are arranged between a final deflection electromagnet and a deflection electromagnet at the incident side thereof so that a parallel irradiation field is formed through the superimposition of kicks caused by the two or more scanning electromagnets.

With regard to a particle beam irradiation apparatus utilizing a rotating gantry, Patent Document 3 discloses a configuration in which an electromagnet for moving an irradiation field is disposed at the upstream side of a deflection electromagnet and a pair of X-direction and Y-direction scanning electromagnets are arranged at the downstream side of the deflection electromagnet so that the electromagnet for moving an irradiation field largely moves the irradiation field and in the moved region, the scanning electromagnets scan a beam in the X direction and the Y direction.

PRIOR ART REFERENCE

[Patent Document]

[Patent Document 1] Japanese Patent Application Laid-Open No. 2008-154627 (Paragraph [0024] and FIG. 2)

[Patent Document 2] Japanese Patent Application Laid-Open No. 2002-22900

[Patent Document 3] Japanese Patent Application Laid-Open No. H8-257148

DISCLOSURE OF THE INVENTION

Problems to be Solved by the Invention

In the particle beam irradiation system disclosed in FIG. 2 of Patent Document 1, in the case where the scanning speed of a particle beam is made high-speed, a large-capacity scanning electromagnet power source is required in proportion to the inductances and the scanning speeds of the scanning electromagnets X and Y. Accordingly, the capacity of the power source for the particle beam irradiation system increases in proportion to a required irradiation field size (proportional to an irradiation target size) and a required scanning speed. Moreover, in the particle beam irradiation apparatus disclosed in Patent Document 2, a particle beam is scanned with a plurality of scanning electromagnets; however, because the configuration thereof is characterized in that a parallel irradiation field where a charged particle beam is irradiated in a parallel manner at an irradiation position is formed, the flexibility in forming an irradiation is small. Furthermore, the particle beam irradiation apparatus disclosed in Patent Document 3 is configured in such a way that an irradiation field is largely moved by disposing at the upstream side an electromagnet for moving an irradiation field and a scanning electromagnet disposed at the downstream side scans a charged particle beam; therefore, only the idea that the electromagnet for moving an irradiation field and the scanning electromagnet are operated separately from each other has been disclosed.

The objective of the present invention is to provide, in contrast to charged particle beam scanning methods as described above, a particle beam irradiation apparatus that makes a plurality of scanning electromagnets exert their abilities as much as possible to increase the flexibility in scanning a charged particle beam so that scanning of a charged particle beam can be performed with a high accuracy and with a high flexibility in the speed, from a low speed to a high speed.

Means for Solving the Problems

According to the present invention, in a particle beam irradiation apparatus in which an incident charged particle beam is scanned on desired orbits in two directions, i.e., in the X and Y directions, which are perpendicular to the traveling direction of the charged particle beam, so as to be irradiated onto an irradiation subject, there are provided two or more pairs of scanning electromagnets that scan a charged particle beam in the two directions; the desired orbits are given by time-series desired orbit data in which a desired irradiation positions corresponding to time are determined; and command values for each of the two or more pairs of scanning electromagnets are generated based on plural pieces of data obtained by frequency-separating the time-series desired orbit data.

Advantage of the Invention

A particle beam irradiation apparatus according to the present invention makes two or more pairs of scanning electromagnets exert their ability as much as possible, so that an effect, such that scanning of a charged particle beam can be performed with a high accuracy and with a high flexibility from a low speed to a high speed, is demonstrated.

BRIEF DESCRIPTION OF THE DRAWINGS

FIG. 3 is a set of imaginary diagrams for explaining circumstances in which a charged particle beam is scanned by a pair of X-direction and Y-direction electromagnets;

FIG. 14 is a table representing examples of inputs and outputs in FIG. 4;

FIG. 15 is a table representing examples of inputs and outputs in FIG. 13;

FIG. 16 is a table representing various variants and coefficients in the equations (3) and (4);

FIG. 19 is a table representing various variants and coefficients in the equations (5) and (6);

FIG. 20 is a table representing various variants and coefficients in the equations (7) and (8);

BEST MODE FOR CARRYING OUT THE INVENTION

Embodiment 1

Figure 1:
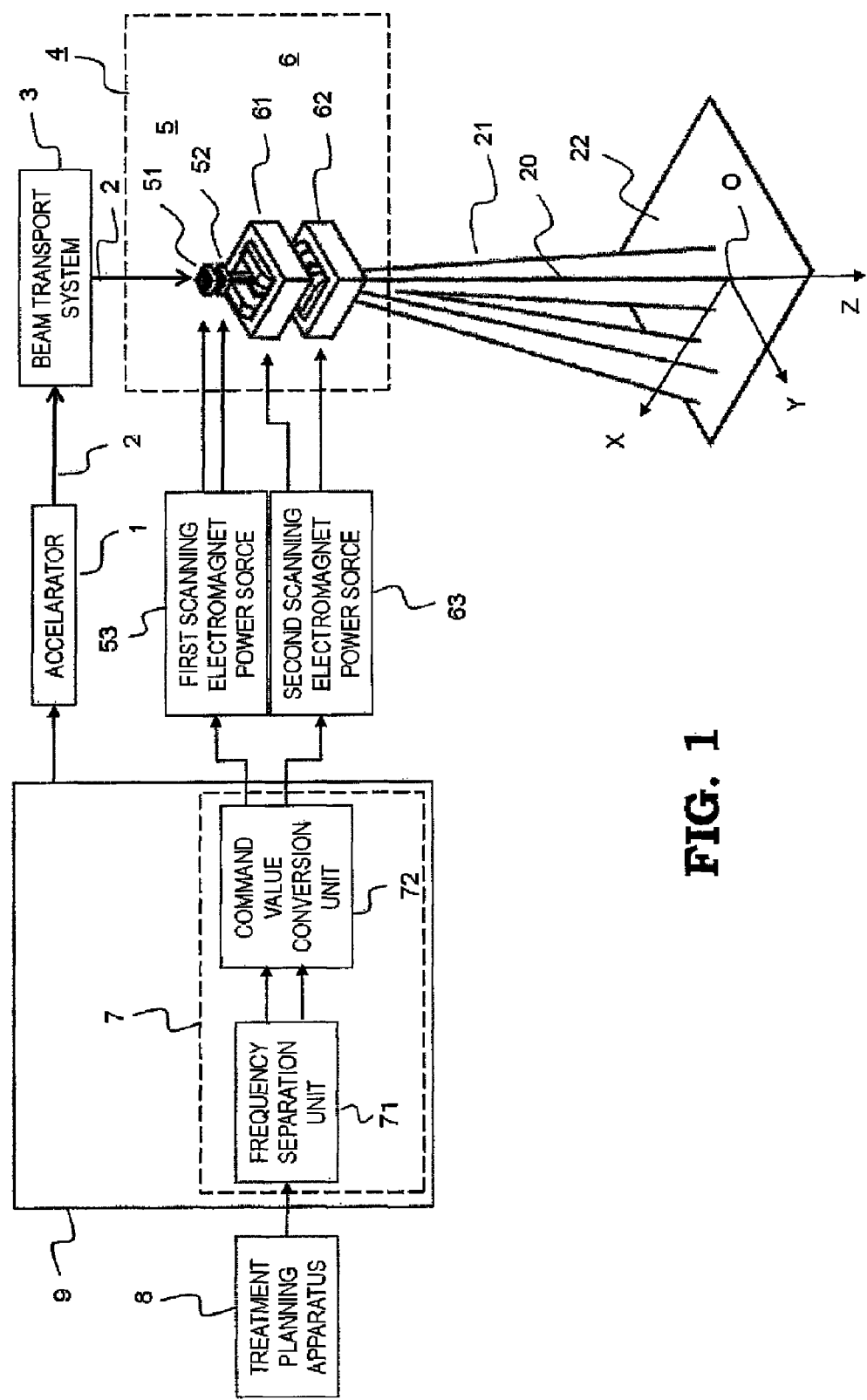
FIG. 1 is a block diagram schematically illustrating the configuration of a particle beam therapy system including a particle beam irradiation apparatus according to Embodiment 1 of the present invention.

FIG. 1 is a block diagram schematically illustrating the configuration of a particle beam therapy system including a particle beam irradiation apparatus according to Embodiment 1 of the present invention. In FIG. 1, an accelerator 1 outputs a charged particle beam 2 such as a proton beam or a carbon beam, and a beam transport system 3 configured with electromagnets, and the like, guides the charged particle beam 2 to a beam irradiation system 4. In the beam irradiation system 4, there are provided two pairs of electromagnets, i.e., a first scanning electromagnet 5 and a second scanning electromagnet 6 that each scan the incident charged particle beam 2 on a two dimensional plane of the X-Y direction, which is a direction perpendicular to the traveling direction of the charged particle beam 2. The first scanning electromagnet 5 includes an X-direction scanning electromagnet 52 and a Y-direction scanning electromagnet 51; the second scanning electromagnet 6 includes an X-direction scanning electromagnet 62 and a Y-direction scanning electromagnet 61. As described above, each of the first scanning electromagnet 5 and the second scanning electromagnet 6 is configured with a set of two electromagnets, i.e., an X-direction scanning electromagnet and a Y-direction scanning electromagnet. The respective excitation coils of the first scanning electromagnet 5 are driven by a first scanning electromagnet power source 53; the respective excitation coils of the second scanning electromagnet 6 are driven by a second scanning electromagnet power source 63. A cooperative control scanning control unit 7 provided in a particle beam therapy system controller 9 that controls the whole particle beam therapy system including the accelerator 1, the beam irradiation system 4, and the like controls the first scanning electromagnet power source 53 and the second scanning electromagnet power source 63 in such a way that the first scanning electromagnet 5 and the second scanning electromagnet 6 cooperatively scan a charged particle beam. For example, from a treatment planning apparatus 8 that generates data when a treatment is planned, the cooperative control scanning control unit 7 receives time-series data on positions which are irradiated with a charged particle beam; when therapy is performed (or therapy is prepared), the time-series data is frequency-separated by a frequency separation unit 71 and then is converted by a command value conversion unit 72 into excitation-current command values for the excitation coils that are driven by the first scanning electromagnet power source 53 and the second scanning electromagnet power source 63. A charged particle beam 21 scanned by the first scanning electromagnet 5 and the second scanning electromagnet 6 is irradiated onto a predetermined position of an irradiation subject 22 at a predetermined time.

In this situation, the region where a charged particle beam is scanned by the first scanning electromagnet 5 is narrower than the region where the charged particle beam is scanned by the second scanning electromagnet 6. That is to say, the angle up to which the first scanning electromagnet 5 deflects a charged particle beam (the maximum deflection angle of the first scanning electromagnet 5) is smaller than the angle up to which the second scanning electromagnet 6 deflects the charged particle beam (the maximum deflection angle of the second scanning electromagnet 6). In general, the smaller the deflection angle of a scanning electromagnet is, the smaller the magnetic field generated by the electromagnet may be; a small electromagnet, i.e., an electromagnet which requires a small current to flow therein and whose inductance is small, may be utilized. Accordingly, as the first scanning electromagnet 5, an electromagnet whose inductance is smaller than that of the second scanning electromagnet 6 can be adopted. For example, the first scanning electromagnet 5 can be formed of an air-core coil; thus, the structure of the first scanning electromagnet 5 is simplified. Because the magnetic field of an electromagnet having a small inductance can rapidly be changed, the magnetic field of the first scanning electromagnet 5 can faster be changed than that of the second scanning electromagnet 6. Expressing with electrical characteristics, in comparison to the second scanning electromagnet 6, the first scanning electromagnet 5 is fast and has a high-frequency response characteristics, as a frequency response.

In FIG. 1, the first scanning electromagnet 5 having a smaller maximum deflection angle is disposed at a more upstream side of the charged particle beam 2 than the second scanning electromagnet 6 having a larger maximum deflection angle. In general, the size of an electromagnet can be decreased in proportion to the maximum deflection angle thereof; when the opening where a charged particle beam enters each electromagnet is taken into consideration, it is more preferable to dispose at a more upstream side the first scanning electromagnet 5 having a smaller maximum deflection angle, because the positioning and the size of the electromagnet can more readily be designed. In this regard, however, it may also be allowed to dispose at a more upstream side of the charged particle beam 2 the second scanning electromagnet 6 having a larger maximum deflection angle.

Figure 2:
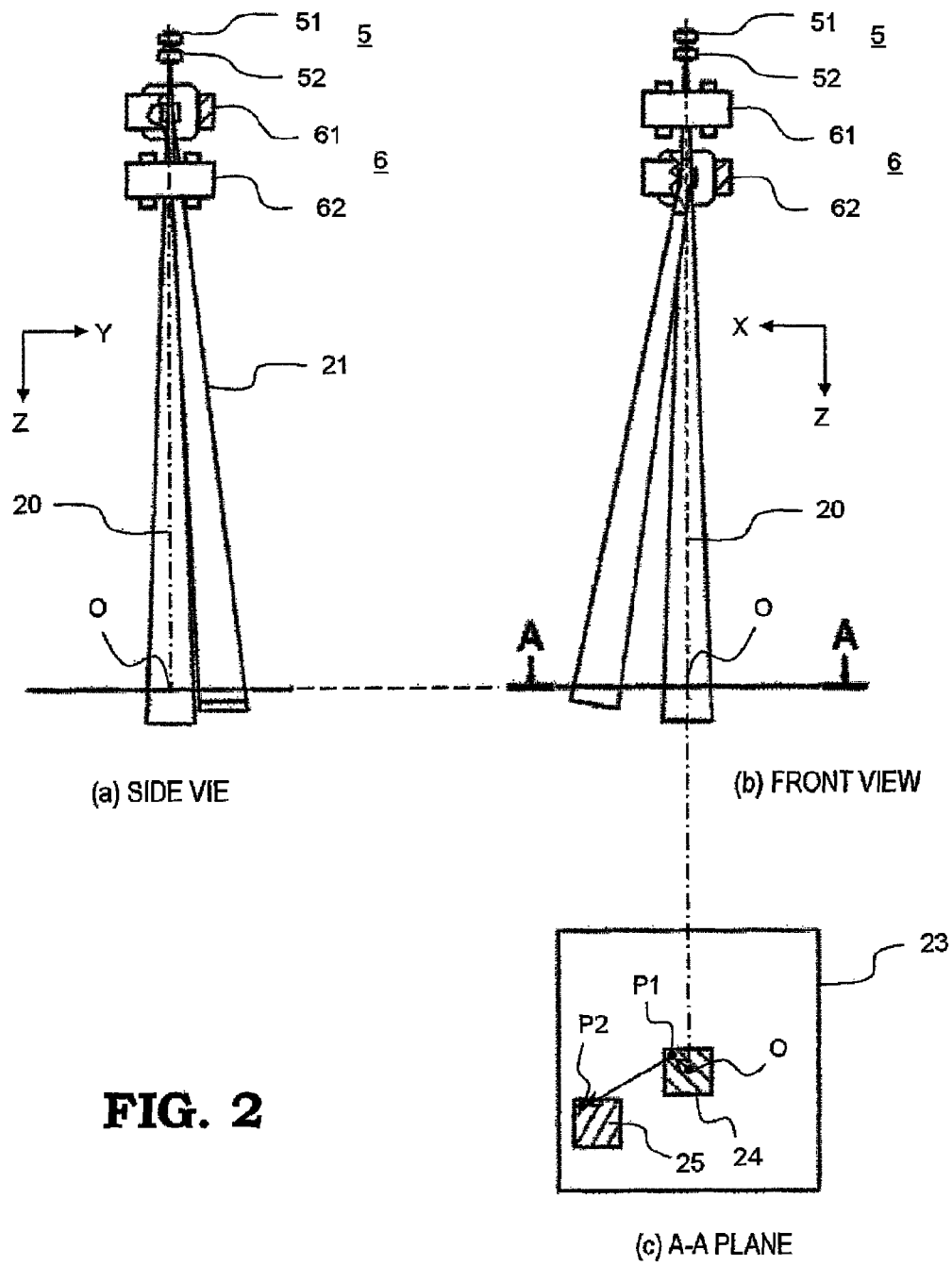
FIG. 2 is a set of schematic diagrams illustrating circumstances in which a charged particle beam is scanned by a particle beam irradiation apparatus according to Embodiment 1 of the present invention.

FIG. 2 is a set of schematic diagrams illustrating circumstances in which a charged particle beam is scanned by the particle beam irradiation apparatus illustrated in FIG. 1; FIG. 2(a) is a side view which shows the Y direction. FIG. 2(b) is a front view which shows the X direction. FIG. 2(c) is a view illustrating the scanning range of a charged particle beam and the like as viewed along the A-A plane in FIG. 2(b). FIG. 3 is a set of image diagrams for explaining circumstances in which a charged particle beam is scanned by a pair of X-direction and Y-direction electromagnets. FIG. 3(A) is a bird's eye view; FIG. 3(B) is a set of a front view and a side view expressing the bird's eye view. For example, in the first scanning electromagnet 5, the Y-direction scanning electromagnet 51 that scans a charged particle beam in the Y direction is disposed at an upstream side, and the X-direction scanning electromagnet 52 that scans a charged particle beam in the X direction is disposed at a downstream side. The incident charged particle beam 2 is firstly deflected in the Y direction with respect to an action axis 100 of scanning, for the charged particle beam, that is performed by the Y-direction scanning electromagnet 51 at the upstream side. The deflected charged particle beam is deflected in the X direction with respect to an action axis 200 of scanning, for the charged particle beam, that is performed by the X-direction scanning electromagnet 52 at the upstream side. In such a way as described above, a charged particle beam is irradiated onto a region that spreads out in the two (X-Y) dimensions. In Embodiment 1 of the present invention, the scanning illustrated in FIG. 3 is performed at two stages.

Hereinafter, the operation of a particle beam irradiation apparatus according to Embodiment 1 of the present invention will be explained with reference to FIGS. 1 and 2. At first, the constituent apparatuses are aligned in such a way that when the first scanning electromagnet 5 and the second scanning electromagnet 6 do not operate, i.e., when a charged particle beam is deflected by none of these scanning electromagnets, the charged particle beam is irradiated onto an isocenter O, which is a reference point. Reference numeral 20 denotes the beam axis of the charged particle beam in this situation. The beam axis 20 represents a trajectory on which a charged particle beam travels when the first scanning electromagnet 5 and the second scanning electromagnet 6 do not operate. In addition, in order to determine the irradiation position of a charged particle beam, a coordinate system is established. For example, as illustrated in FIG. 1, with respect to the isocenter O, as an origin, the X and Y axes are set in directions that are perpendicular to the beam axis, and the Z axis is set in the direction of the beam axis. X, Y, and Z in FIG. 2 represent only the directions.

The incident charged particle beam 2 is scanned in the two-dimensional (X-Y) direction by the first scanning electromagnet 5 and the second scanning electromagnet 6. Setting of a beam irradiation position in the Z direction is performed by adjusting the energy of a charged particle so as to change the range, i.e., by changing and controlling the position of a Bragg peak. In this case, the irradiation position in the Z direction is represented by a representative point in the distribution of irradiated doses, for example, the position of a Bragg peak.

The beam irradiation position is set on the isocenter O under the condition that the first scanning electromagnet 5 and the second scanning electromagnet 6 do not operate. Here, a range in which a beam can be scanned when only the first scanning electromagnet 5 is operated will be considered. As illustrated in FIG. 3, a beam can be scanned in a range that spreads out in a sector shape in the Y-axis direction caused by the Y-direction scanning electromagnet 52. Caused by the Y-direction scanning electromagnet 51, a beam can be scanned in a range spreading out in a sector shape in the X-axis direction. As a result, the scannable range becomes the scanning area (default), of the first scanning electromagnet 5, that is a region 24 illustrated by slanted lines in FIG. 2(c).

Next, it will be explained how the scanning area 24 changes when the second scanning electromagnet 6 at the downstream is operated. Caused by the Y-direction scanning electromagnet 61, a beam is also scanned in a range spreading out in a sector shape in the Y-axis direction. In addition, caused by the X-direction scanning electromagnet 62, a beam is scanned in a range spreading out in a sector shape in the X-axis direction. Eventually, the scanning area moves to a region 25 illustrated by slanted lines in FIG. 2(c). In addition, the scannable area becomes a region 23 when both the first scanning electromagnet 5 and the second scanning electromagnet 6 are operated.

In the case where only the first scanning electromagnet 5 is operated and a certain command value is inputted, the beam irradiation position moves from O to $P_1$. In this situation, the travel amount $OP_1$ of the beam irradiation position is a travel amount caused by only the first scanning electromagnet 5. Then, when the second scanning electromagnet 6 is operated and a certain command value is inputted, the final beam irradiation position moves to $P_2$. The eventual travel amount $OP_2$ of the beam irradiation position can be expressed as in the following equation.

$$OP_2 = OP_1 + P_1 P_2 \quad (1)$$

In other words, the beam travel amount can be divided into a portion thereof caused by the first scanning electromagnet 5 and a portion thereof caused by the second scanning electromagnet 6.

Figure 4:
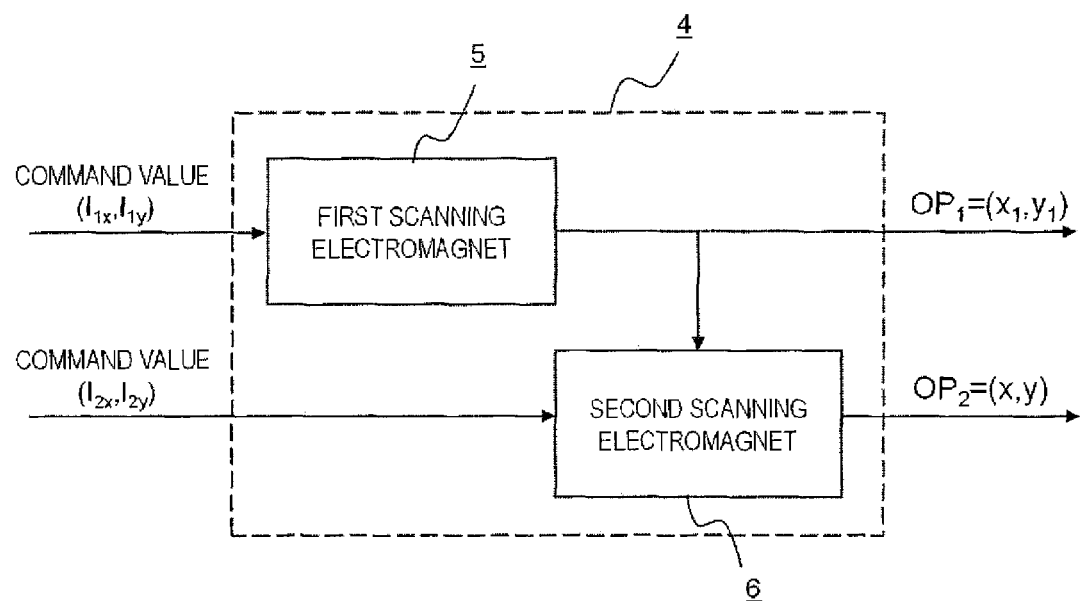
FIG. 4 is a block diagram for explaining the relationship between the command value for a scanning electromagnet and the travel amount of a charged particle beam.

FIG. 4 pictorially expresses the foregoing explanation with a block diagram. In FIG. 4, a command value, which is the input, is the value of an excitation current for the excitation coil of a scanning electromagnet; the output is the travel amount, of the beam irradiation position, that is produced by driving the scanning electromagnet through the value of the excitation current. FIG. 4 represents that when the command value of the first scanning electromagnet 5 is ($I_{1x}$, $I_{1y}$), the travel amount caused by the first scanning electromagnet 5 is $OP_1$, and when the command value of the second scanning electromagnet 6 is ($I_{2x}$, $I_{2y}$), the eventual travel amount of the beam irradiation position is $OP_2$ (the coordinates (x, y) of the beam irradiation position $P_2$). As described above, when the respective command values for the scanning electromagnets are determined, $OP_1(x_1, y_1)$ and $OP_2(x, y)$ are uniquely given. This can be considered as a four-input four-output map that is determined by a physical phenomenon.

Meanwhile, what is significant in a real therapy is an eventual beam irradiation position. A treatment planning apparatus calculates for each patient the position onto which a beam is irradiated and the dose to be irradiated. Furthermore, based on the result of the calculation by the treatment planning apparatus, the desired orbit for the beam irradiation position is calculated.

In the case where there exists only one pair of scanning electromagnets, even only giving the desired orbit for a beam irradiation position suffices; however, because in the present invention, there exist two or more pairs of scanning electromagnets, the solution for obtaining the desired orbit is not unique. That is to say, for the realization of a certain beam irradiation position, there exist an infinite number of roles to be played by the first scanning electromagnet 5 and the second scanning electromagnet 6. This is because there exist an infinite number of combinations of $OP_1$ and $P_1 P_2$ that satisfy $OP_2$ (the left-hand side) of the equation (1).

Figure 5:
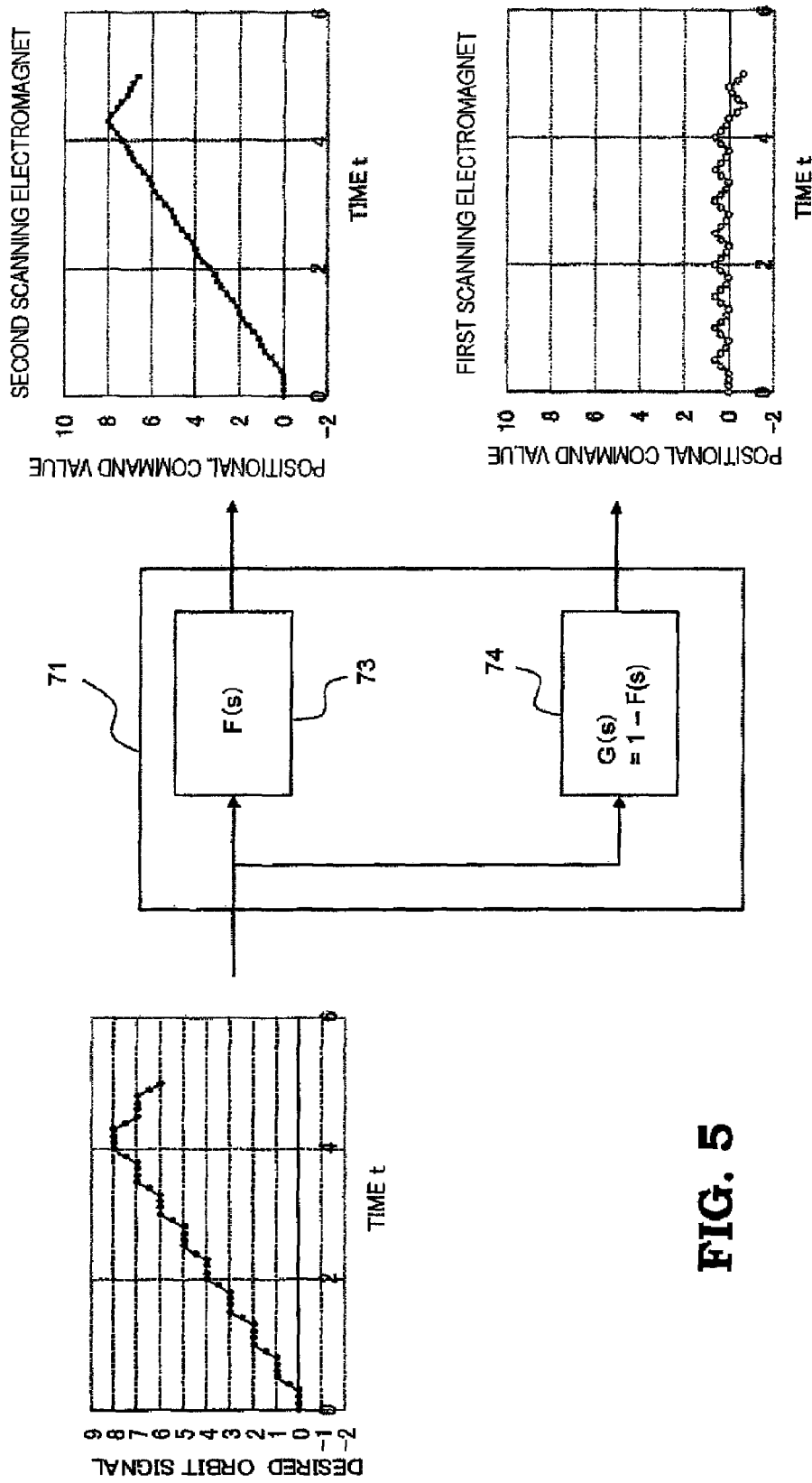
FIG. 5 is a block diagram of the frequency separation unit of a particle beam irradiation apparatus according to Embodiment 1 of the present invention.

FIG. 5 is a block diagram illustrating the frequency separation unit 71 in the cooperative control scanning control unit 7 according to Embodiment 1 of the present invention. The desired orbit transmitted from the treatment planning apparatus is data in which desired irradiation positions corresponding to time are sequentially arranged. In other words, the desired orbit is, for example, such time-series data (signal) as represented at the left side of FIG. 5. The signal in FIG. 5 is represented in a single-coordinate system; however, the signal has the X-coordinate component and the Y-coordinate component. The foregoing desired orbit is an example of desired orbit according to a spot scanning irradiation method in which there is repeated operation of retaining a beam at a predetermined position for a given time and irradiating the beam and then moving the beam to another position, where the beam is retained for the given time and is irradiated, so that the beam is irradiated onto a wide region. In order to obtain positional command values for the first scanning electromagnet 5 and the second scanning electromagnet 6, for example, the following processing is applied to the foregoing desired orbit, taking the characteristics of the first scanning electromagnet 5 and the second scanning electromagnet 6 into consideration. The desired orbit signal, which is an input to the frequency separation unit 71 and is represented at the left side of FIG. 5, is separated, with a filter, into the component for the first scanning electromagnet 5 and the component for the second scanning electromagnet 6. The first scanning electromagnet 5 is of a small size and of a high speed and hence is provided with higher-frequency response characteristics; thus, the first scanning electromagnet 5 is in charge of the high-frequency components of the desired orbit. The second scanning electromagnet 6 is of a large size and of a large scanning width and hence is provided with lower-frequency response characteristics; thus, the second scanning electromagnet 6 is in charge of the low-frequency components of the desired orbit. FIG. 5 shows that the desired orbit signal is separated with a filter. In this situation, the desired orbit that is eventually obtained should be the same as that planned originally. Accordingly, as represented in FIG. 5, a complementary filter (F(s)+G(s)=1) is utilized in this embodiment.

Figure 6:
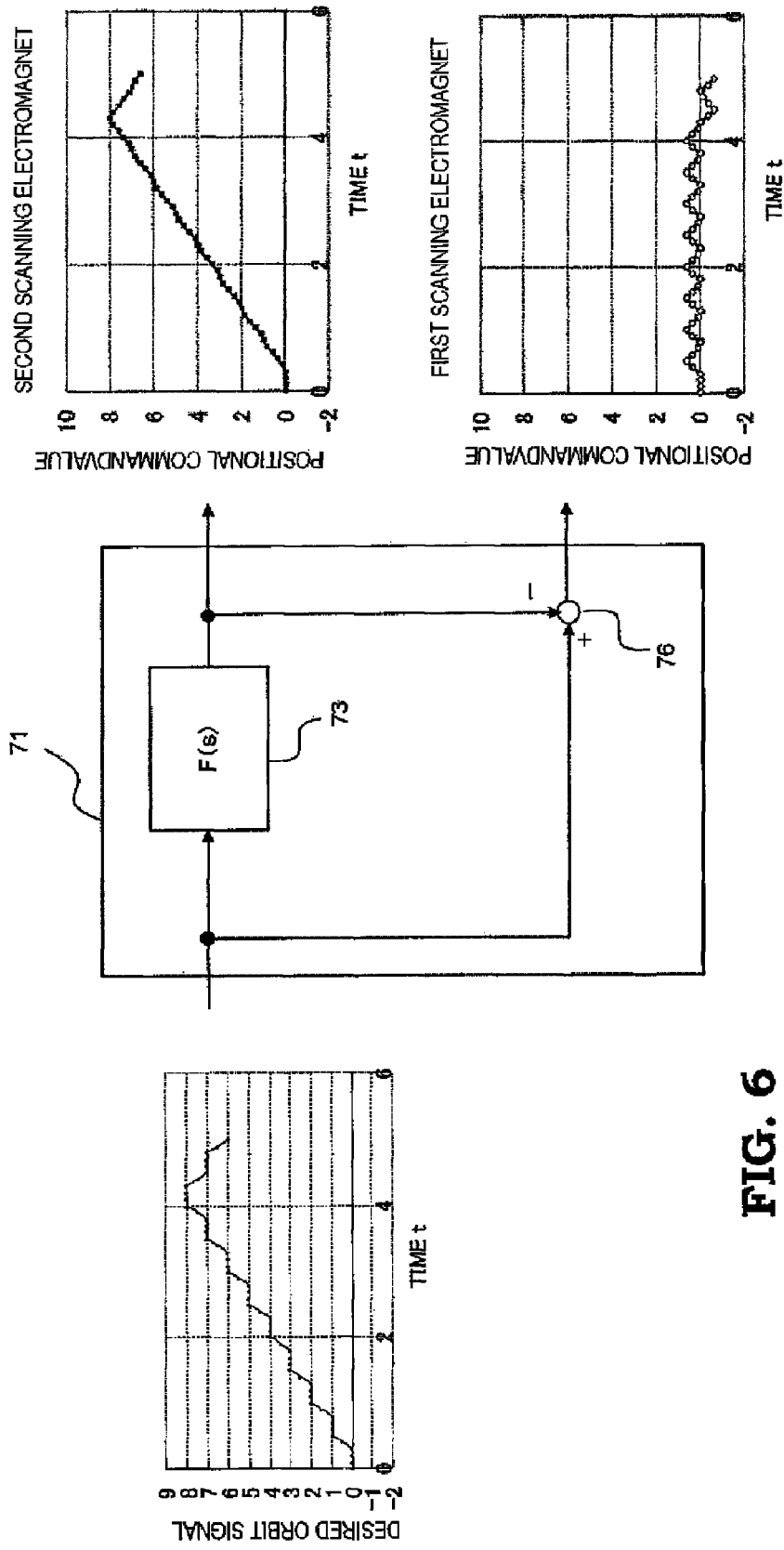
FIG. 6 is a block diagram of another frequency separation unit of a particle beam irradiation apparatus according to Embodiment 1 of the present invention.

In FIG. 5, F(s) is a lowpass filter 73 for the second scanning electromagnet 6; G(s) (=1−F(s)) is a high-pass filter 74 for the first scanning electromagnet 5. Two signals represented at the right side of FIG. 5 are desired orbit signals (positional command values) obtained through separation by these filters. It may be allowed that as represented in FIG. 6, without providing a high-pass filter, only the lowpass filter 73 is provided and the high-frequency components are obtained by subtracting, with a computing unit 76, the low-frequency-component signal separated by the lowpass filter 73 from the desired orbit signal, which is an input signal. In contrast, it may be allowed that without providing a lowpass filter, only a high-pass filter is provided and the low-frequency components are obtained by subtracting the high-frequency-component signal separated by the high-pass filter from the desired orbit signal, which is an input signal.

Figure 7:
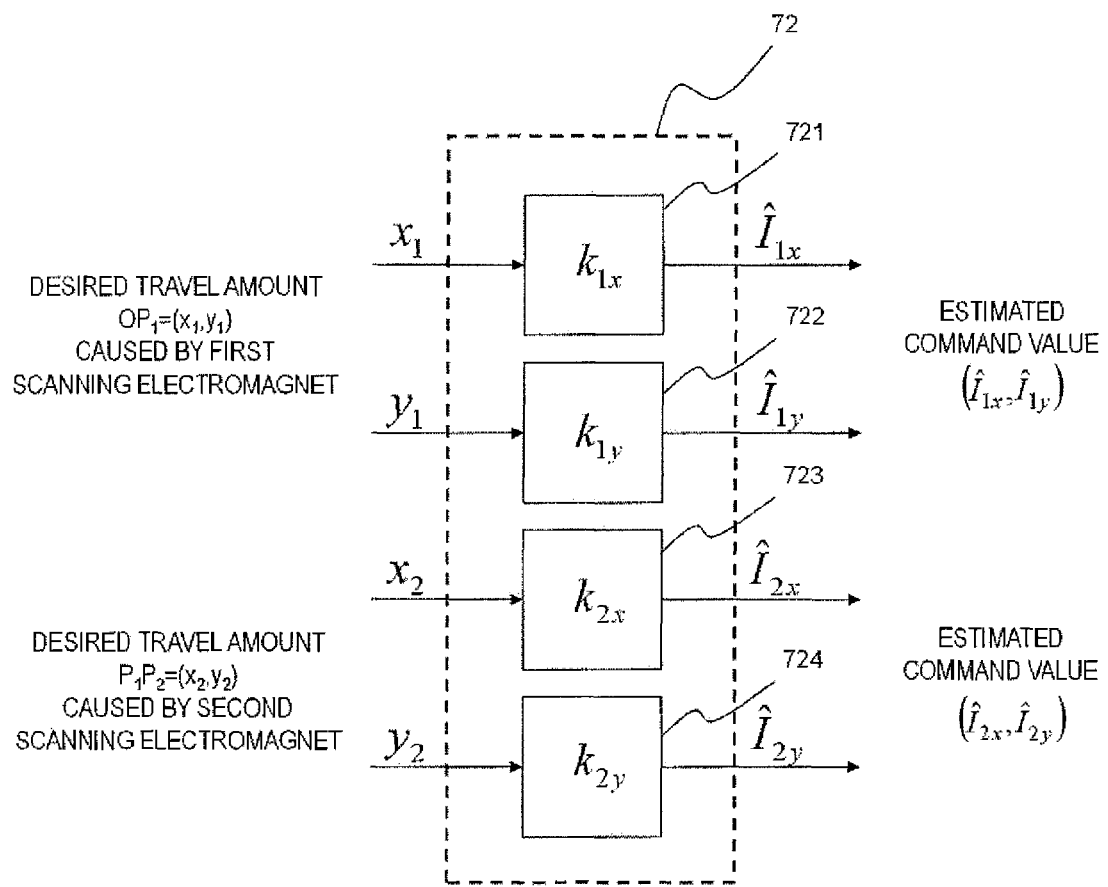
FIG. 7 is a block diagram of the command value conversion unit of a particle beam irradiation apparatus according to Embodiment 1 of the present invention.

The command value conversion unit 72 outputs, as command values, respective excitation currents for the scanning electromagnets in such a way that the respective beam positions through the scanning electromagnets become equal to the respective positional command values; then, the command value conversion unit 72 controls the first scanning electromagnet power source 53 and the second scanning electromagnet power source 63. FIG. 7 illustrates the configuration of a simplest command value conversion unit 72. The command value conversion unit 72 obtains, through a linear approximation, the relationship between the desired irradiation coordinates and the excitation current command value for the scanning electromagnet; the respective estimated command values for the electromagnets are calculated in command value calculation units 721 through 724. For example, the command value calculation unit 721, which calculates an estimated command value for X-direction electromagnet of the first scanning electromagnet, obtains the estimated command value according to the equation (2).

$$\hat{I}_{1x} = k_{1x} x_1 \quad (2)$$

where $k_{1x}$, which is a proportional constant, is the gradient of a straight line obtained through a linear approximation.

Figure 8:
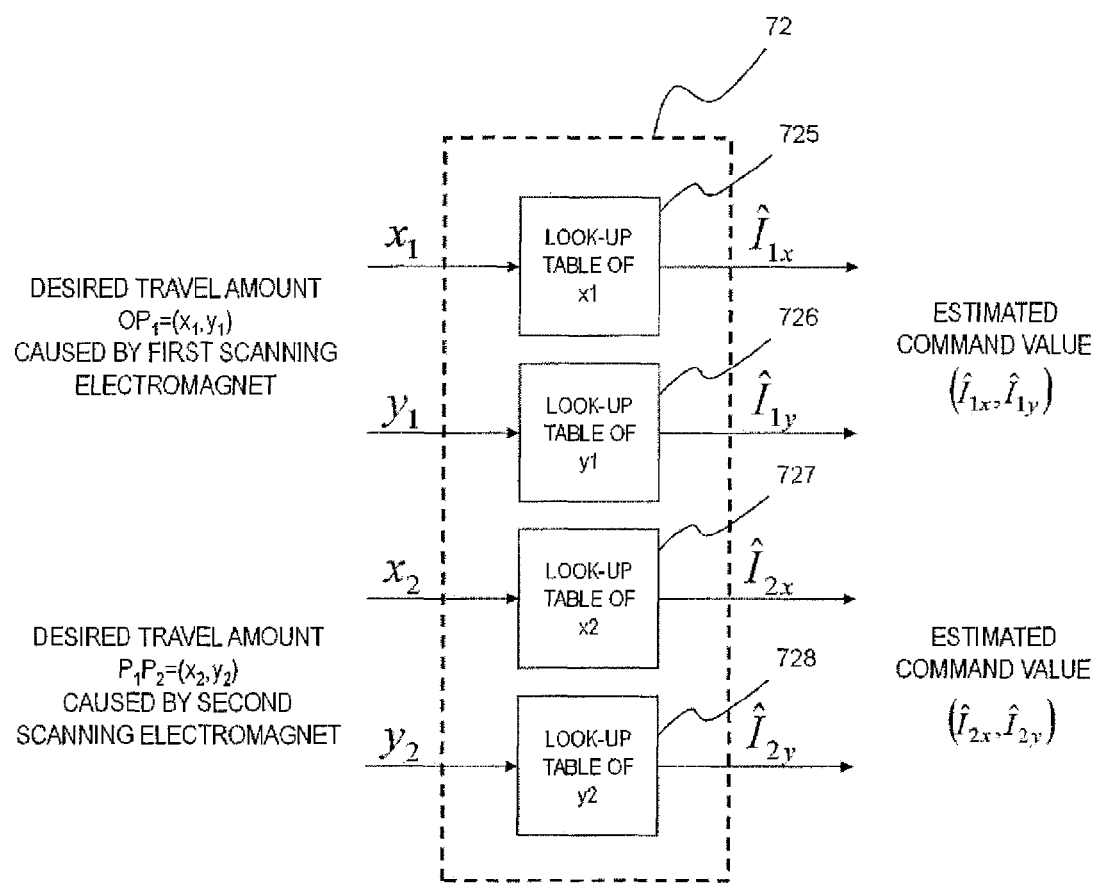
FIG. 8 is a block diagram of another command value conversion unit of a particle beam irradiation apparatus according to Embodiment 1 of the present invention.

FIG. 8 is a block diagram illustrating another example of command value conversion unit 72. Each of Reference numerals 725 through 728 is a look-up table (quick conversion table) in which the relationship between the desired irradiation coordinates and the excitation current command values for the scanning electromagnets are retained as a table. In the case where the linear approximation cannot obtain a sufficient accuracy for the relationship between the desired irradiation coordinates and the excitation current command value for the scanning electromagnet, a broken line approximation is performed so that the result of conversion can be obtained from the look-up table. These command value conversion (creation) methods are typical ones; however, in terms of the positional accuracy, they should be improved. The optimal command value conversion (creation) method will be described later in Embodiment 5.

In this embodiment, a case where a desired orbit is obtained through a spot scanning irradiation method has been described; however, the particle beam irradiation apparatus according to Embodiment 1 of the present invention is not limited to a desired orbit obtained through the spot scanning irradiation method, but can be applied to various desired orbits. Accordingly, a particle beam irradiation apparatus according to Embodiment 1 makes it possible to generate respective command values, for electromagnets, that are required to realize various desired orbits with two pairs of scanning electromagnets, with a simple configuration only to frequency-separate a desired orbit signal; thus, scanning of a charged particle beam can be performed with a high flexibility in the speed, from a low speed to a high speed. Moreover, in the case where the foregoing particle beam irradiation apparatus is applied to a particle beam therapy system, an appropriate desired orbit for each patient can be formed, and scanning can be performed, taking into consideration the characteristics of the scanning electromagnets in each pair; therefore, the scanning time can be reduced.

Embodiment 2

Figure 9:
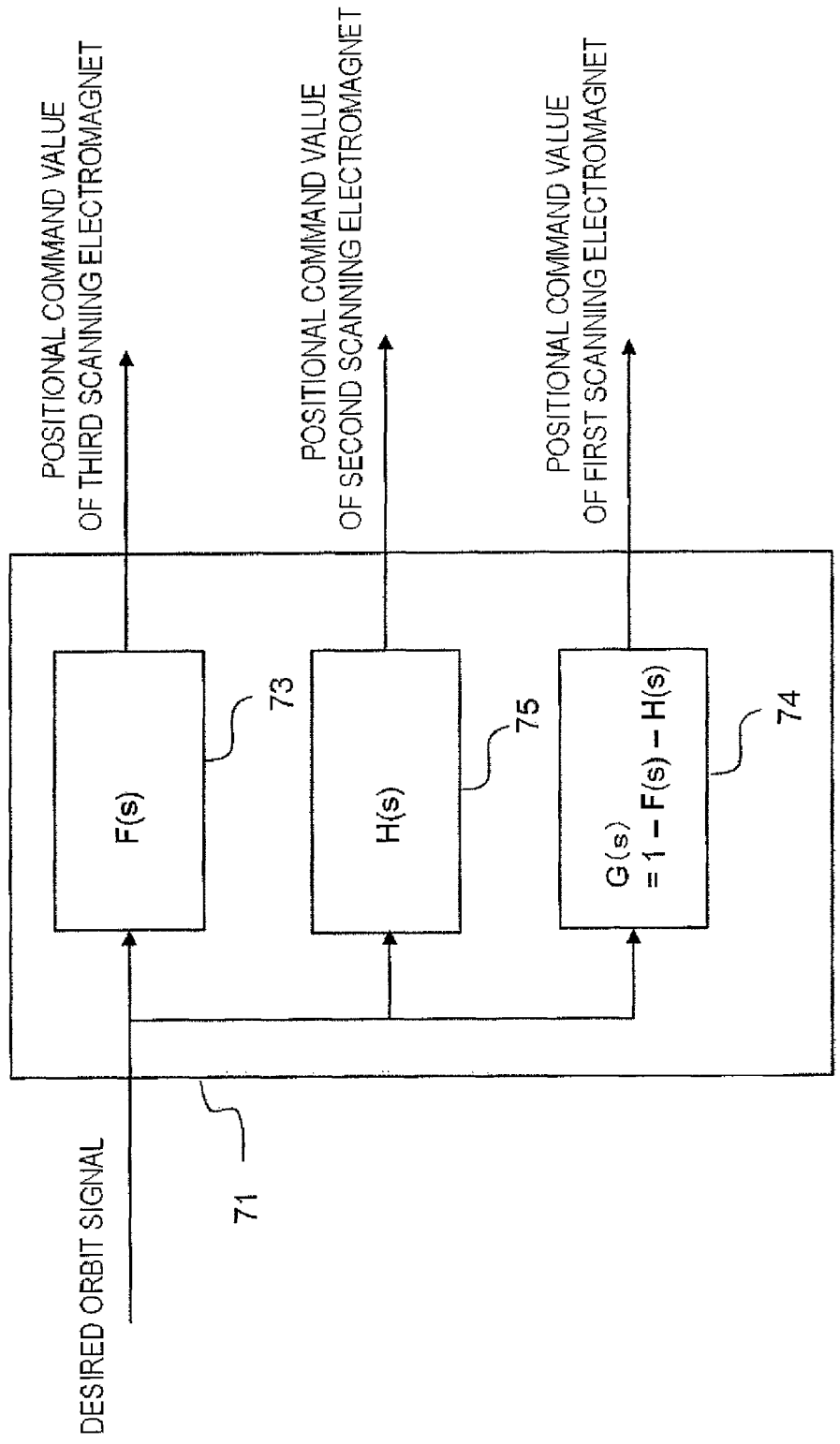
FIG. 9 is a block diagram of the frequency separation unit of a particle beam irradiation apparatus according to Embodiment 2 of the present invention.

FIG. 9 is a block diagram illustrating the configuration of a frequency separation unit 71 in a cooperative control scanning control unit 7 of a particle beam irradiation apparatus according to Embodiment 2 of the present invention. In Embodiment 1, two pairs of scanning electromagnets are utilized; however, in Embodiment 2, three pairs of scanning electromagnets, i.e., a first scanning electromagnet, a second scanning electromagnet, and a third scanning electromagnet are arranged in the beam irradiation system 4 in FIG. 1, from an upstream side to a downstream side of a charged particle beam. For example, the first scanning electromagnet is an electromagnet that has a small maximum deflection angle but can rapidly change the magnetic field; the third scanning electromagnet is an electromagnet that has a large maximum deflection angle and hence can perform a wide-region scanning but that can change the magnetic field only at a low speed; the second scanning electromagnet is an electromagnet that has a maximum deflection angle and a magnetic field changing speed that are characteristically intermediate between the maximum deflection angle and the magnetic field changing speed of the first scanning electromagnet and the maximum deflection angle and the magnetic field changing speed of the third scanning electromagnet. Accordingly, there come the first scanning electromagnet, the second scanning electromagnet, and the third scanning electromagnet, when they are arranged in ascending order of the inductance thereof; the respective frequency response characteristics of the electromagnets are different from one another.

In the case where a charged particle beam is scanned with these three scanning electromagnets, the frequency separation unit 71 in the cooperative control scanning control unit 7 divides a desired orbit signal received from the treatment planning apparatus 8 into the positional command values for the three pairs of scanning electromagnets. In that case, as illustrated in FIG. 9, the desired orbit signal is divided with three filters. In FIG. 9, F(s) is a lowpass filter 73 for the third scanning electromagnet; H(s) is a band-pass filter 75 for the second scanning electromagnet; G(s) (=1−F(s)−H(s)) is a high-pass filter 74 for the first scanning electromagnet. The command value conversion unit 72 outputs, as command values, respective excitation currents for the scanning electromagnets in such a way that the respective command values become equal to the respective desired orbit signals (positional command values) separated by these filters; then, the command value conversion unit 72 controls the first, second, and third scanning electromagnets.

In addition, as is the case with explanation made in Embodiment 1, even in the case where any one of the lowpass filter 73, the band-pass filter 75, and the high-pass filter 74 is omitted, a signal the same as the signal to be separated through the omitted filter can be obtained, by subtracting signals separated through the other two filters from the desired orbit signal.

As described above, in Embodiment 2, a case where three pairs of scanning electromagnets are utilized has been explained; however, further more pairs of scanning electromagnets can be utilized. As described above, the present invention can be applied to a case where two or more pairs of scanning electromagnets are utilized and makes it possible to generate, with a simple configuration, respective command values, for electromagnets, that are required to realize various desired orbits with two pairs of scanning electromagnets; thus, scanning of a charged particle beam can be performed with a high flexibility in the speed, from a low speed to a high speed.

Embodiment 3

Figure 10:
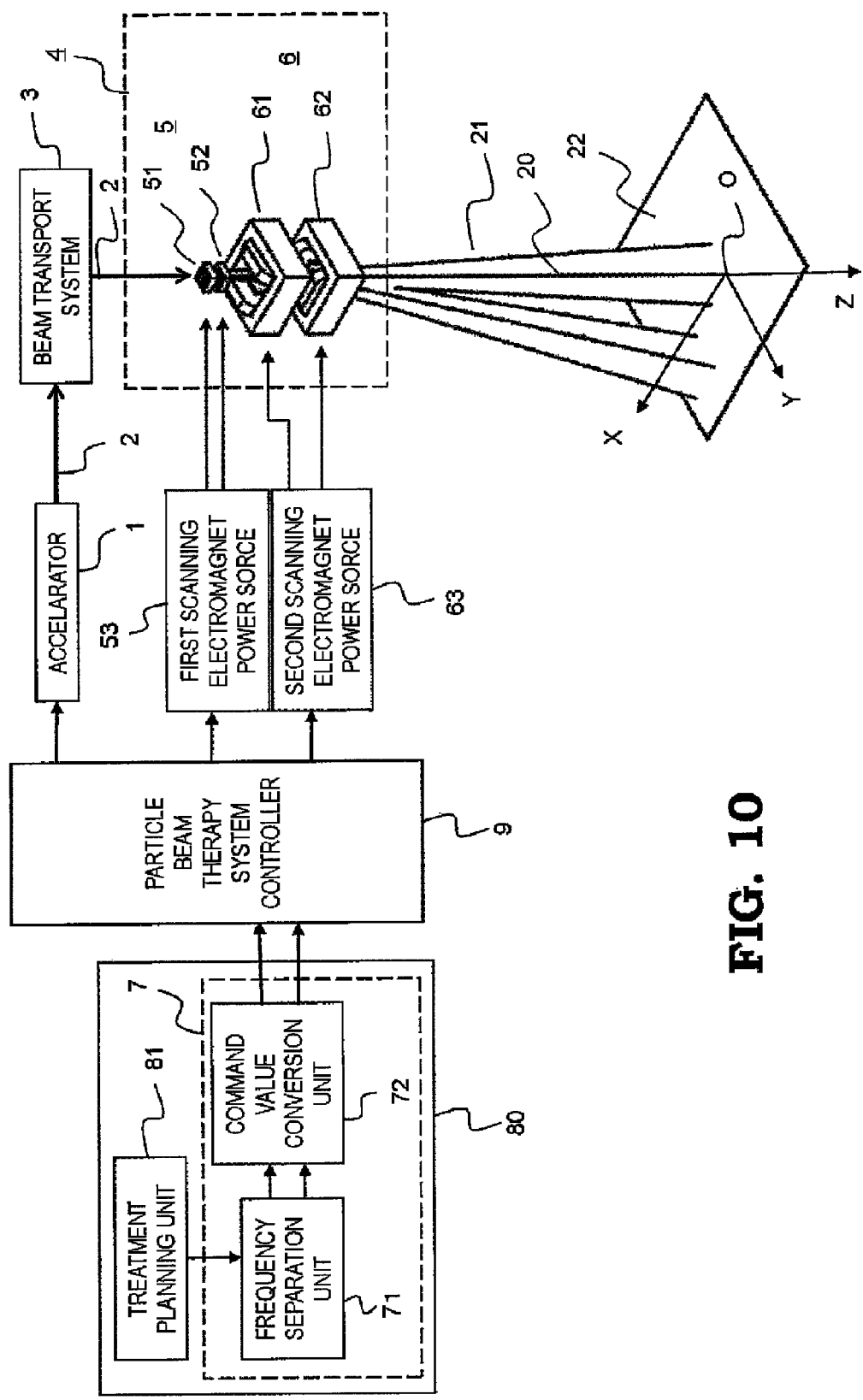
FIG. 10 is a block diagram schematically illustrating a particle beam irradiation apparatus according to Embodiment 3 of the present invention.

FIG. 10 is a block diagram schematically illustrating the configuration of a particle beam irradiation apparatus according to Embodiment 3 of the present invention. In FIG. 10, the same reference numerals as those in FIG. 1 denote the same or equivalent elements. In Embodiment 1, a desired orbit signal outputted from the treatment planning apparatus 8 is temporarily transmitted to and stored in the particle beam therapy system controller 9; when therapy is performed, the desired orbit signal is frequency-separated with filters in the cooperative control scanning control unit 7 provided in the particle beam therapy system controller 9; then, positional command values for the first scanning electromagnet 5 and the second scanning electromagnet 6 are generated in real time. In Embodiment 3, in a treatment planning apparatus 80, there is provided the cooperative control scanning control unit 7 that has a function of creating command values for the first scanning electromagnet power source 53 and the second scanning electromagnet power source 63. From a treatment planning unit 81 in the treatment planning apparatus 8, the cooperative control scanning control unit 7 receives a desired orbit signal; the desired orbit signal is frequency-separated by filters in the frequency separation unit 71 so that respective positional command values for the first scanning electromagnet 5 and the second scanning electromagnet 6 are generated; then, these positional command values are converted by the command value conversion unit 72 into respective command values for the scanning electromagnet power sources. That is to say, when a treatment plan is made, the treatment planning apparatus 80 preliminarily generates respective command values for the first scanning electromagnet 5 and the second scanning electromagnet 6.

As described above, in any of the units, there may be performed a process in which a desired orbit signal generated according to a treatment plan is frequency-separated by filters so that respective command values for the scanning electromagnets are generated. It may be allowed that the frequency separation unit 71, explained in each of Embodiments 1 and 2, is provided in a computer provided in a conventional particle beam irradiation apparatus.

Embodiment 4

Figure 11:
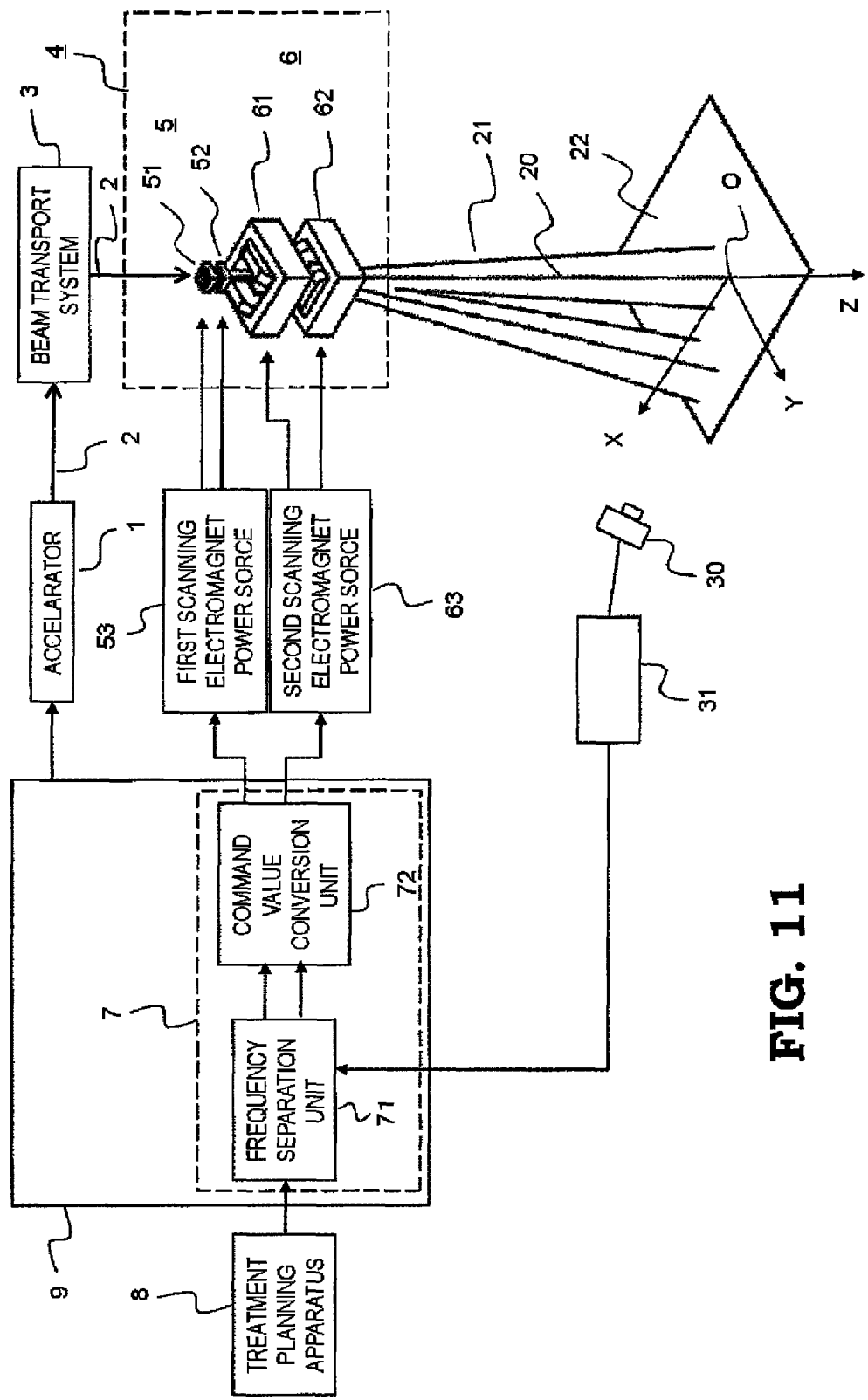
FIG. 11 is a block diagram schematically illustrating the configuration of a particle beam irradiation apparatus according to Embodiment 4 of the present invention.
Figure 12:
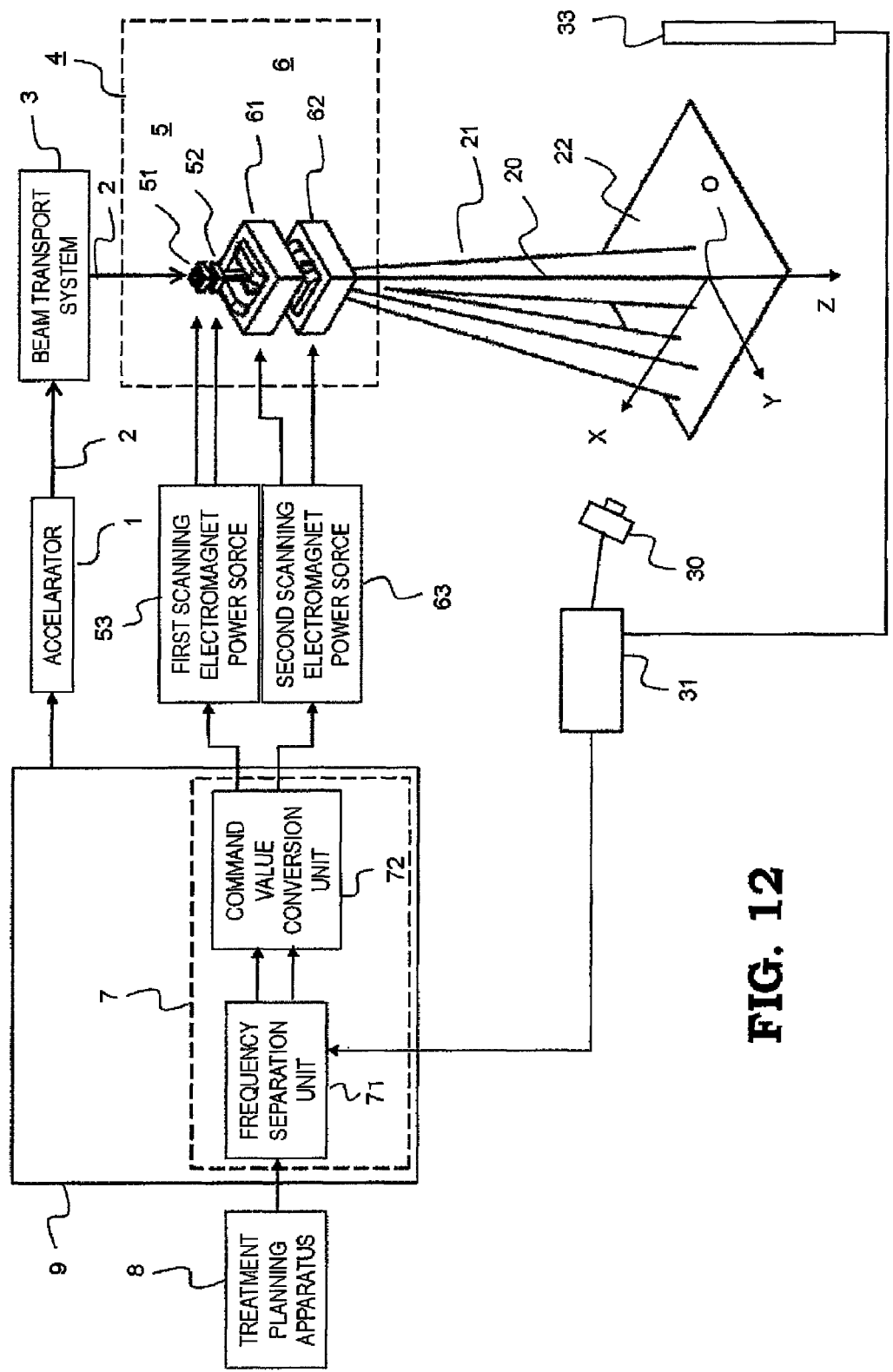
FIG. 12 is a block diagram schematically illustrating the configuration of another particle beam irradiation apparatus according to Embodiment 4 of the present invention.

In Embodiment 4, it will be explained that the present invention can be applied also to a case where a diseased site is moved or deformed by respiration or the like. Each of FIGS. 11 and 12 is a block diagram schematically illustrating a particle beam irradiation apparatus according to Embodiment 4 of the present invention. In FIGS. 11 and 12, the same reference numerals as those in FIG. 1 denote the same or equivalent elements. In a therapy utilizing a particle beam therapy system, a diseased site which is an irradiation subject may be moved or deformed by physiological activities of a patient such as respiration. Accordingly, for the purpose of performing effective and safe therapy, various contrivances such as "respiration-synchronized irradiation" and "diseased site tracking irradiation" are proposed.

FIG. 11 is a diagram illustrating the configuration of a particle beam therapy system provided with a camera 30 for monitoring the movement of a patient's body surface. In addition, in FIG. 11, only a single camera system is illustrated; however, in general, two or more camera systems are utilized because the objective thereof is to obtain three-dimension positional information on a diseased site. A plurality of marks are preliminarily put on the body surface of a patient, and by utilizing these marks as landmarks, three-dimension positional information is obtained by an image processing device 31. Based on the three-dimension positional information obtained by the image processing device 31, the cooperative control scanning control unit 7 estimates the position and the posture of a diseased site and modifies the desired irradiation position. The desired irradiation position modified by the cooperative control scanning control unit 7 is also frequency-separated by the frequency separation unit 71; therefore, the position of a beam can be controlled through cooperation between the first scanning electromagnet and the second scanning electromagnet.

FIG. 12 is a diagram illustrating the configuration of a particle beam therapy system configured for the purpose the same as that of the particle beam therapy system illustrated in FIG. 11. In FIG. 12, an X-ray image-capturing device configured with an FPD (Flat Panel Detector) 33, an X-ray control device 34 including an image processing function, and the like, are utilized. In addition, in FIG. 12, only a single X-ray image-capturing device is illustrated; however, in general, two or more X-ray image-capturing devices are utilized because the objective thereof is to obtain three-dimension positional information on a diseased site. By utilizing an X-ray image-capturing device, a transparent image including a diseased site and its periphery can be obtained. Accordingly, in this case, the landmarks are portions having a characteristic bone shape and the like. The flow including and after the process in which the X-ray control device 34 obtains the three-dimension positional information on a landmark is the same as the flow in FIG. 11, described above.

The particle beam therapy system according to Embodiment 4 is configured in such a way that as described above, the movement of a diseased site, which is an irradiation subject, is detected, and in accordance with the movement, a desired irradiation position is corrected, i.e., feedback compensation is performed; therefore, higher-accuracy irradiation can be realized.

Embodiment 5

In each of Embodiments 1 through 4, in a beam irradiation system comprising a plurality of scanning electromagnets, how to determine respective desired scanning amounts of respective scanning electromagnets for generating respective command values which are given to respective scanning electromagnets has been explained. Specifically, respective amounts of beam scanning to be undertaken by the scanning electromagnets are generated with filters in such a way that a given desired orbit is eventually achieved. It may seemingly be considered that when respective amounts of beam scanning to be undertaken by the scanning electromagnets are determined, it is easy to generate respective command values for the scanning electromagnets. However, even when the amounts of beam scanning are determined, it is not easy, in fact, to accurately obtain command values (the values of excitation currents) for the scanning electromagnets that achieve the amounts of beam scanning. In particular, because the scanning electromagnet disposed at a downstream side is affected by the scanning electromagnet disposed at an upstream side, generation of the command value for the scanning electromagnet disposed at a downstream side requires contrivance. Thus, in Embodiment 5, a problem such that a command value for achieving the desired orbit cannot readily be obtained will be explained in detail; then, a means for solving the problem will be explained.

With reference to FIG. 4 described in Embodiment 1, a technical problem, such that the command value for the scanning electromagnet and achieving the desired orbit cannot be obtained easily, will be explained. The left portion of FIG. 4 suggests that command values are inputted to the scanning electromagnets (cause). The right portion of FIG. 4 suggests that as a result, a beam is scanned (the irradiation position is moved) and then a uniquely determined irradiation position is outputted (result). As a whole, this physical phenomenon can be considered as a four-input four-output "map".

In addition, this phenomenon is just like the idea that the result is attributed to the cause, i.e., the order in the "causality principle"; therefore, the foregoing map will particularly be referred to as a "forward-direction map" or a "forward map". In this regard, however, the "command value" here denotes the following matter. A control amount for driving a scanning electromagnet is a current, in general. Accordingly, the command value here denotes the desired value of a control amount, and is, in general, given in units of current.

Figure 13:
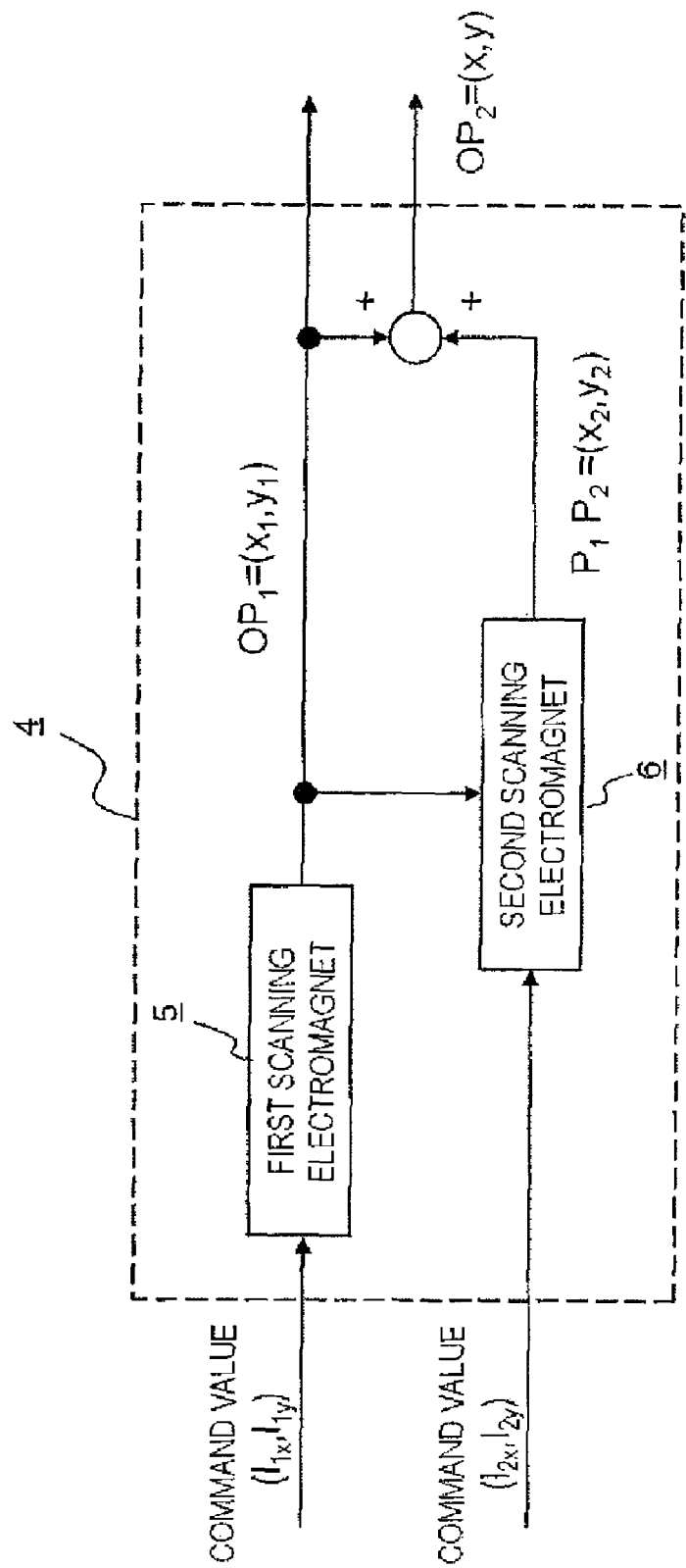
FIG. 13 is a block diagram, other than FIG. 4, for explaining the relationship between the command value for a scanning electromagnet and the travel amount of a charged particle beam.

This physical phenomenon can be interpreted as the one illustrated in FIG. 13 in addition to the one illustrated in FIG. 4. The inputs and outputs in FIG. 4 are set as in Table 1 represented in FIG. 14. As represented in Table 1, four outputs are obtained from four inputs; therefore, a four-input, four-output map is produced. Meanwhile, the output 1 and the output are determined depending only on the first scanning electromagnet, i.e., depending only on the input 1 and input 2; therefore, partially, the map is two-input and two-output. However, as a whole, the map can be regarded as being four-input and four-output. When any two vectors among three vectors $OP_1$, $OP_2$, and $P_1P_2$ are given, the rest one can be calculated according to the equation (1). In the forward map represented in FIG. 4, the outputs are two vectors $OP_1$ and $OP_2$; however, as represented in FIG. 13, the outputs of the forward map may be two vectors $OP_1$ and $P_1P_2$. Table 2 in FIG. 15 represents the inputs and outputs of the map represented in FIG. 13.

Here, Example 1, a simple example, for explaining a technical problem will be described. It is assumed that a beam is being scanned with a given scanning amount and is irradiated onto a given irradiation position. In the foregoing circumstances, there will be considered a case where with the scanning electromagnet disposed at a downstream side, the irradiation position is moved, for example, by +1 cm in the X direction. In this situation, depending on where the scanning electromagnet at an upstream side is scanning the beam, the amount of control, by the scanning electromagnet at the downstream side, which is required to achieve the foregoing amount of moving varies. That is to say, the command value for moving by +1 cm in the X direction the irradiation position of a beam that is located at the origin while the scanning electromagnet at the upstream side does not work is different from the command value for further moving by +1 cm (=11 cm) in the X direction the irradiation position of a beam that is located, for example, at a position shifted from the origin by 10 cm in the X direction while the scanning electromagnet at the upstream side works. Empirically, a phenomenon in which the foregoing difference in the command value is caused has been known.

Example 2, another simple example, for explaining a technical problem will be described. It is assumed that the control amount for the X-direction scanning electromagnet at the upstream side, that is required to move the irradiation position of a beam located at the origin while the scanning electromagnet at the downstream side does not work to a position whose X coordinate is 2 cm, is 2[A]. In addition, it is assumed that the control amount for the X-direction scanning electromagnet at the downstream side, that is required to move the irradiation position of a beam located at the origin while the scanning electromagnet at the upstream side does not work to a position whose X coordinate is 2 cm, is 2[A]. In this situation, in the case where the control amount 2[A] is given to the X-direction scanning electromagnet at the upstream side and the control amount 2[A] is given to the X-direction scanning electromagnet at the downstream side, the irradiation position of the beam is not necessarily a position whose X coordinate is 4 cm. In fact, it is not likely to be 4 cm. Empirically, a phenomenon in which the foregoing difference in the beam irradiation position is caused has been known.

As described above, it is required that the concept of the control amount (current), which is the cause of a physical phenomenon, and the concept of the beam position, which is the result of the physical phenomenon, are always made clear and distinguished from each other. Example 1, described above, is an example showing that the addition principle with regard to the result (beam position) is not satisfied by the corresponding cause (control amount). Example 2 is an example showing that the addition principle with regard to the cause (control amount) is not satisfied by the corresponding result (beam position). This matter is caused because the forward map representing the physical phenomenon is not linear.

As what shows the difficulty in creating a precise command value, the following point also needs to be taken into consideration. The scanning electromagnets are mounted in such a way as to scan a beam in the X direction and the Y direction that are perpendicular to the beam axis. Ideally, it is desirable that the X coordinate component of a beam position can be realized only by the X-direction scanning electromagnet and the Y coordinate component of the beam position can be realized only by the Y-direction scanning electromagnet. However, in reality, it is difficult to perform perfectly independent control of the X coordinate component and the Y coordinate component of a beam irradiation position. For example, it has empirically been known that when under the condition that a beam is scanned by the Y-direction scanning electromagnet in such a way that the Y coordinate of the beam position becomes 3 cm, the beam is scanned by the X-direction scanning electromagnet, the trajectory of the beam irradiation position does not become completely parallel to the X axis, and the beam position shifts from the position whose Y coordinate is 3 cm. As one of the causes for the above phenomenon, an error in mounting the scanning electromagnet is conceivable; however, the cause is not limited to it. The phenomenon that as described above, the X coordinate component and the Y coordinate component of a beam position cannot independently be controlled by a single scanning electromagnet is expressed as that "there exists an interference term", "there exists a cross term between X and Y", or the like.

The problem of the interference term between X and I is appeared even in a case of where a pair of scanning electromagnets scans a beam. In the beam irradiation system 4 according to the present invention, at least two pairs of scanning electromagnets, i.e., the first scanning electromagnet 5 at an upstream side and the second scanning electromagnet 6 at a downstream side, are utilized. Therefore, the problem of the interference term between X and Y becomes further complicated in the present invention. Before considering a case where there exist two or more pairs of scanning electromagnets, a case where there exists a pair of X-direction and Y-direction scanning electromagnets will be described.

As described above, the problem of the interference term between X and Y in a case of a pair of scanning electromagnet has been found out as an objective. In order to solve the problem, the command value conversion unit 72 has X-direction and Y-direction inverse-map formula models in which the X-direction command value for the X-direction scanning electromagnet and the Y-direction command value for the Y-direction scanning electromagnet are generated for realizing the irradiation of the beam using the desired irradiation position coordinates of a charged particle beam. The X-direction and Y-direction inverse-map formula models are configured in such a way as to include two variants, where the desired irradiation position coordinates on the irradiation position plane of a charged particle beam are expressed by the two variants.

It will be explained how the inverse-map formula model at a time when a pair of scanning electromagnets is assumed corresponds to the inverse-map formula model at a time when two pairs of scanning electromagnets are assumed. As described above, the travel amount $OP_1$ of a beam caused by the first scanning electromagnet 5 depends only on the first scanning electromagnet 5. Accordingly, in the concept of the map in each of FIGS. 4 and 13, $OP_1$ is two-input and two-output. In other words, it may be considered that also in the beam irradiation system configured with two pairs of scanning electromagnets, the portion where the command value for the first scanning electromagnet 5 is inputted to the first scanning electromagnet and then $OP_1$ is outputted is similar to the forward map representing the physical phenomenon of the beam irradiation system configured with a pair of scanning electromagnets.

In contrast, the beam travel amount $P_1P_2$ (the output of the map in FIG. 13) caused by the second scanning electromagnet 6 situated at the downstream side of the first scanning electromagnet 5 and the eventual beam travel amount $OP_2$ (the output of the map in FIG. 4) each depend on both the first scanning electromagnet 5 and the second scanning electromagnet 6. Accordingly, it can be said that the map that outputs the beam travel amount $P_1P_2$ caused by the second scanning electromagnet 6 is partially four-input and two-output (FIG.

13, Table 2: from Input 1, Input 2, Input 3 and Input 4 to Output 3 and Output 4). Alternatively, it can be said that the map that outputs the eventual beam travel amount $OP_2$ is partially four-input and two-output (FIG. 4, Table 1: from Input 1, Input 2, Input 3 and Input 4 to Output 3 and Output 4). It can be said that this part is characteristic of the beam irradiation system utilizing two pairs of scanning electromagnets. As a whole, it can be said that the forward map that represents the physical phenomenon of the beam irradiation system configured with two pairs of scanning electromagnets, which output $OP_1$ and $P_1P_2$ or $OP_1$ and $OP_2$, is four-input and four-output.

The physical phenomenon "forward map" suggests that when a command value is determined and given to the scanning electromagnet, the beam irradiation position is uniquely determined; in each of FIGS. 4 and 13, the order thereof is shown by the arrows. However, what is actually required as the function of an apparatus is that a desired beam irradiation position is given at first and then the command value, for the scanning electromagnet, that is required to realize the desired beam irradiation position is obtained. That is to say, an approach whose direction is opposite to that of the physical phenomenon is required.

Also in the case of a beam irradiation system having a pair of scanning electromagnets, a similar opposite-direction approach is required. In order to achieve the approach that is opposite to the physical phenomenon, the command value conversion unit 72 is provided with an inverse-map formula model. As the inverse-map formula model, for example, such polynomial-structure ones as described below are conceivable.

$$\hat{I}_{1x} = a_{00} + a_{01}x_1 + a_{10}y_1 + a_{02}x_1^2 + a_{11}x_1y_1 + a_{20}y_1^2 \tag{3}$$

$$\hat{I}_{1y} = b_{00} + b_{01}x_1 + b_{10}y_1 + b_{02}x_1^2 + b_{11}x_1y_1 + b_{20}y_1^2 \tag{4}$$

where the variants and the coefficients are as represented by Table 3 in FIG. 16.

In addition, the equations (3) and (4) show polynomial expressions having the highest order of 2; however, which highest order and what terms are to be adopted may appropriately be determined in accordance with the nonlinearity level of the map. In this specification, the inverse-map utilized in the command value conversion unit 72 is not limited to the equation (3) or (4).

Meanwhile, in order to obtain the estimation value of a command value with the equation (3) or (4), it is required that the unknown parameters (the coefficients in the polynomial expression) are preliminarily determined. For example, trial irradiation is preliminarily performed when no patient is present, and then based on data obtained by actual measurement, the unknown parameters can be obtained through the least square method or the weighted least square method. Such work as described above will be referred to as calibration.

Figure 17:
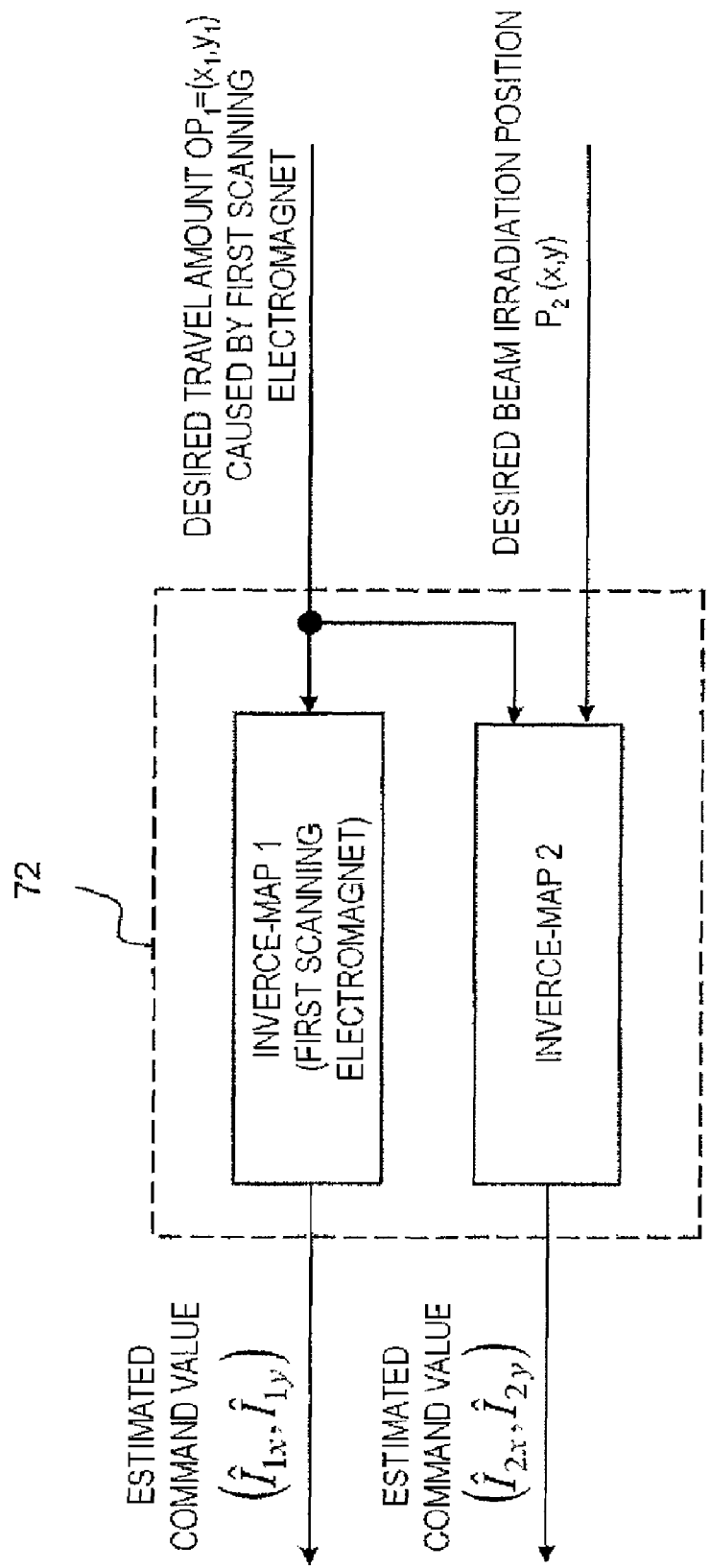
FIG. 17 is a block diagram illustrating an example of command value conversion unit of a particle beam irradiation apparatus according to Embodiment 5 of the present invention.
Figure 18:
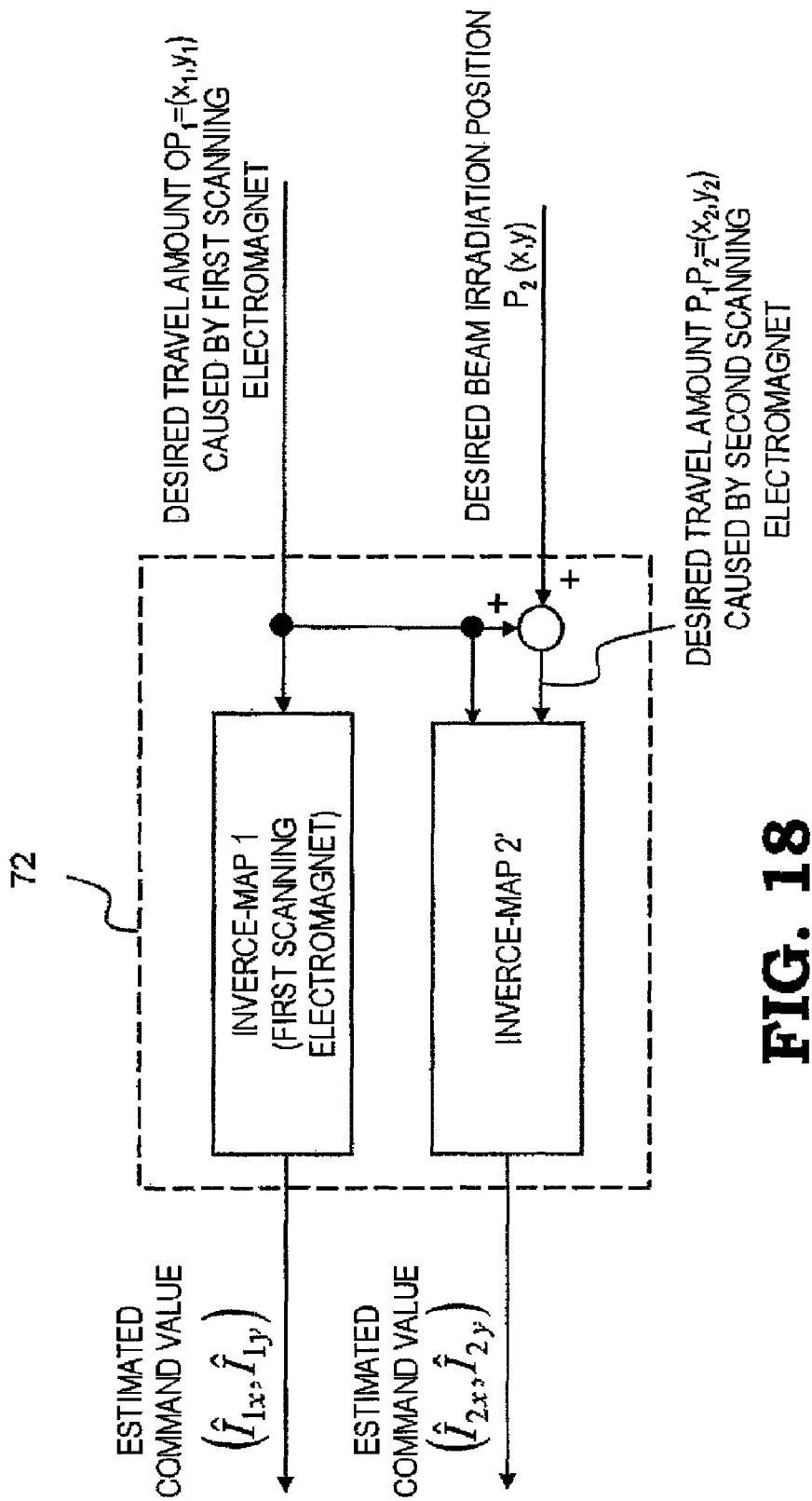
FIG. 18 is a block diagram illustrating another example of command value conversion unit of a particle beam irradiation apparatus according to Embodiment 5 of the present invention.

Each of FIGS. 17 and 18 is a block diagram illustrating an "inverse-map" in which an approach that is opposite to the physical phenomenon is achieved by the command value conversion unit 72, in the case of a beam irradiation system utilizing two pairs of scanning electromagnets. FIG. 17 is a block diagram of an inverse-map corresponding to the forward map illustrated in FIG. 4. FIG. 18 is a block diagram of an inverse-map corresponding to the forward map illustrated in FIG. 13. The command value conversion unit 72 in a particle beam irradiation apparatus according to the present invention is provided with the inverse-map formula model illustrated in FIG. 17 or 18.

As illustrated in FIGS. 17 and 18, it can be seen that the respective inverse-maps 2 for obtaining the estimation value of a command value for the second scanning electromagnet 6 (scanning electromagnet at the downstream side) are four-input and two-output. That is to say, formula models that are different from two-input two-output ones represented in the equations (3) and (4) are required. Thus, in Embodiment 5 of the present invention, formula models described below are utilized.

The inverse-map formula models corresponding to FIG. 17 are, for example, as represented in the following equations (5) and (6).

$$\hat{I}_{2x} = c_{0000} + c_{0001}x_1 + c_{0010}y_1 + c_{0100}x + c_{1000}y + \\ c_{0002}x_1^2 + c_{0011}x_1y_1 + c_{0020}y_1^2 + c_{0101}x_1x + c_{0110}y_1x + \\ c_{0200}x^2 + c_{1001}x_1y + c_{1010}y_1y + c_{1100}xy + c_{2000}y^2 \tag{5}$$

$$\hat{I}_{2y} = d_{0000} + d_{0001}x_1 + d_{0010}y_1 + d_{0100}x + d_{1000}y + \\ d_{0002}x_1^2 + d_{0011}x_1y_1 + d_{0020}y_1^2 + d_{0101}x_1x + d_{0110}y_1x + \\ d_{0200}x^2 + d_{1001}x_1y + d_{1010}y_1y + d_{1100}xy + d_{2000}y^2 \tag{6}$$

where the variants and the coefficients are as represented by Table 4 in FIG. 19.

The inverse-map formula models corresponding to FIG. 18 are, for example, as represented in the following equations (7) and (8).

$$\hat{I}_{2x} = e_{0000} + e_{0001}x_1 + e_{0010}y_1 + e_{0100}x_2 + e_{1000}y_2 + \\ e_{0002}x_1^2 + e_{0011}x_1y_1 + e_{0020}y_1^2 + e_{0101}x_1x_2 + e_{0110}y_1x_2 + \\ e_{0200}x_2^2 + e_{1001}x_1y_2 + e_{1010}y_1y_2 + e_{1100}x_2y_2 + e_{2000}y_2^2 \tag{7}$$

$$\hat{I}_{2y} = f_{0000} + f_{0001}x_1 + f_{0010}y_1 + f_{0100}x_2 + f_{1000}y_2 + \\ f_{0002}x_1^2 + f_{0011}x_1y_1 + f_{0020}y_1^2 + f_{0101}x_1x_2 + f_{0110}y_1x_2 + \\ f_{0200}x_2^2 + f_{1001}x_1y_2 + f_{1010}y_1y_2 + f_{1100}x_2y_2 + f_{2000}y_2^2 \tag{8}$$

where the variants and the coefficients are as represented by Table 5 in FIG. 20.

In addition, the equations (5) through (8) show polynomial expressions having the highest order of 2; however, which highest order and what terms are to be adopted may appropriately be determined in accordance with the nonlinearity level of the map. The purport of the present invention is not to limit the inverse-map utilized in the command value conversion unit 72 to the equations (5) through (8).

Also in the case where the estimation value of a command value is obtained with the equation (5) through (8), it is required that the unknown parameters (the coefficients in the polynomial expression) are preliminarily determined. Trial irradiation is preliminarily performed when no patient is present, and then based on data obtained by actual measurement, the unknown parameters are obtained through the least square method or the weighted least square method. In addition, in order to distinguish it from the trial irradiation, irradiation for performing therapy for a patient will be referred to as "proper irradiation". The work (including trial irradiation) for obtaining unknown parameters will be referred to as calibration.

In Embodiment 5, as described above, the cooperative control scanning control unit has the inverse-map model of a forward map which is assumed for an irradiation system provided with two scanning electromagnets in series, and obtains unknown parameters in the inverse-map model from actual data on trial irradiation for calibration. Therefore, the problem, such that the addition principle cannot be performed caused by the nonlinearity in the physical phenomenon (forward map) when a command value for the scanning electromagnet is obtained, can be solved. And the problem of the interference term between X and Y be solved. Furthermore, when a polynomial model is adopted in the inverse-map formula model, Embodiment 5 demonstrates an extra effect such that an addition and a multiplication are only required and hence the estimation value of the command value can rapidly be calculated.

Embodiment 6

Figure 21:
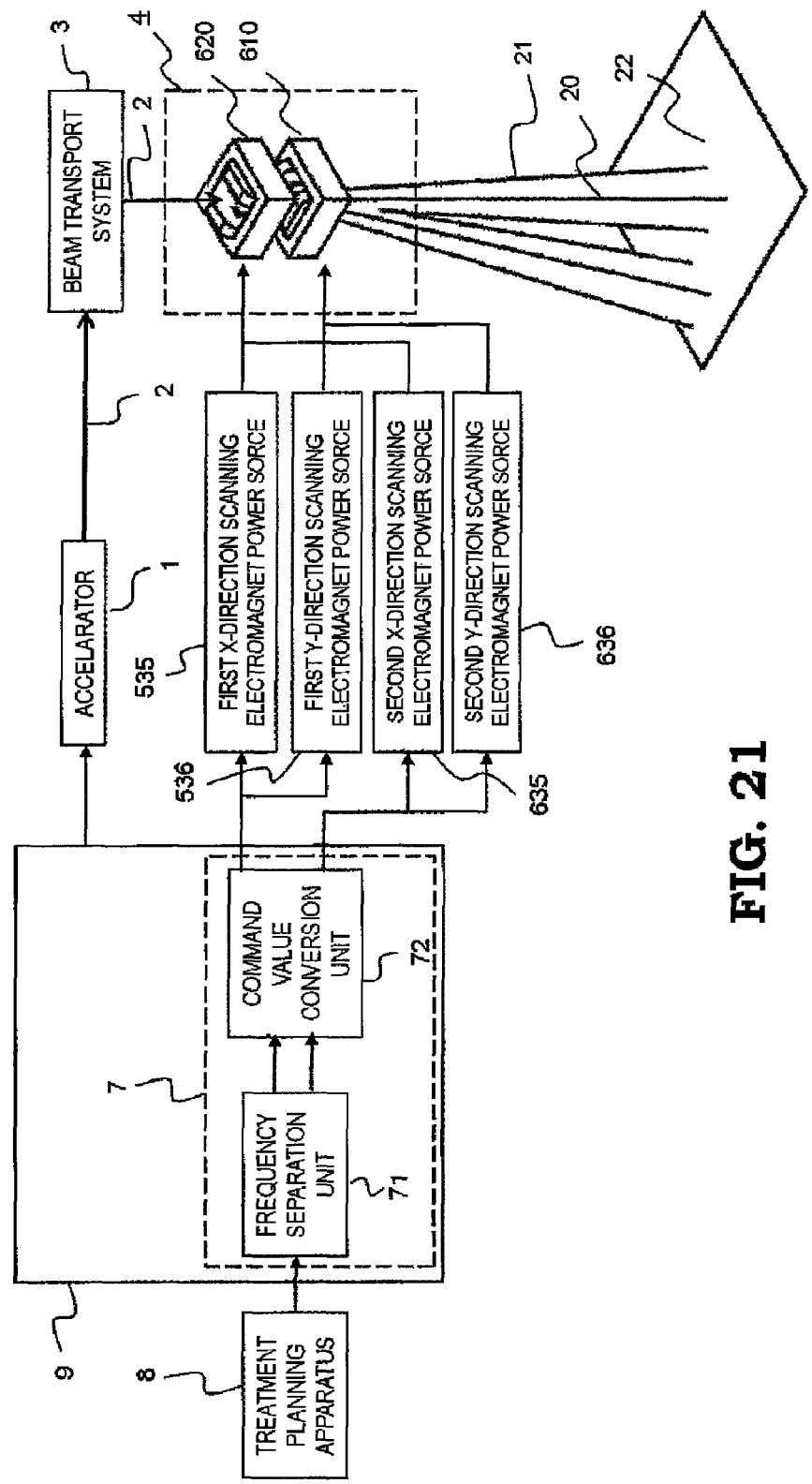
FIG. 21 is a block diagram schematically illustrating the configuration of a particle beam therapy system including a particle beam irradiation apparatus according to Embodiment 6 of the present invention.

FIG. 21 is a block diagram illustrating a particle beam irradiation apparatus according to Embodiment 6 of the present invention. In FIG. 21, the same reference numerals as those in FIG. 1 denote the same or equivalent elements or components. In Embodiment 6, as the scanning electromagnet that deflects the particle beam 2 in the X direction so as to perform scanning, only an X-direction scanning electromagnet 620 is provided. As the scanning electromagnet that deflects the particle beam 2 in the Y direction so as to perform scanning, only a Y-direction scanning electromagnet 610 is provided. There exists only one excitation coil in the X-direction scanning electromagnet 620; this single excitation coil is driven by two power sources, i.e., a first X-direction scanning electromagnet power source 535 and a second X-direction scanning electromagnet power source 635. Similarly, there exists only one excitation coil in the Y-direction scanning electromagnet 610; this single excitation coil is driven by two power sources, i.e., a first Y-direction scanning electromagnet power source 536 and a second Y-direction scanning electromagnet power source 636. As is the case with the X-direction scanning electromagnet 62 of the second scanning electromagnet 6 in Embodiment 1, the X-direction scanning electromagnet 620 has a capability of deflecting the particle beam 2 up to the maximum width of a target. The second X-direction scanning electromagnet power source 635 is a power source that can output a large current, but is low-voltage and hence cannot rapidly change the current because the inductance of the excitation coil of the X-direction scanning electromagnet 620 is large; that is to say, the second X-direction scanning electromagnet power source 635 is a low-voltage large-current power source. The first X-direction scanning electromagnet power source 535 is a high-voltage small-current power source, the value of a current which can output is small, but that can rapidly change the current even when the inductance of the excitation coil of the X-direction scanning electromagnet 620 is large. The current from the first X-direction scanning electromagnet power source 535 and the current from the second X-direction scanning electromagnet power source 635 are superimposed on each other and flow in the excitation coil of the X-direction scanning electromagnet 620.

Similarly, there exists only one excitation coil in the Y-direction scanning electromagnet 610; this single excitation coil is driven by two power sources, i.e., a first Y-direction scanning electromagnet 536 and a second Y-direction scanning electromagnet 636. As is the case with the Y-direction scanning electromagnet 61 of the second scanning electromagnet 6 in Embodiment 1, the Y-direction scanning electromagnet 610 has a capability of deflecting the particle beam 2 up to the maximum width of a target. The second Y-direction scanning electromagnet power source 636 is a power source that can output a large current, but is low-voltage and hence cannot rapidly change the current because the inductance of the excitation coil of the Y-direction scanning electromagnet 610 is large; that is to say, the second Y-direction scanning electromagnet power source 636 is a low-voltage large-current power source. The first Y-direction scanning electromagnet power source 536 is a high-voltage small-current power source, the value of a current which can output is small, but that can rapidly change the current even when the inductance of the excitation coil of the Y-direction scanning electromagnet 610 is large. The current from the first Y-direction scanning electromagnet power source 536 and the current from the second Y-direction scanning electromagnet power source 636 are superimposed on each other and flow in the excitation coil of the Y-direction scanning electromagnet 610.

In the particle beam irradiation apparatus according to Embodiment 6, the first X-direction scanning electromagnet power source 535 and the X-direction scanning electromagnet 620 perform operation corresponding to the operation of the first scanning electromagnet power source 53 and the X-direction scanning electromagnet 52 of the first scanning electromagnet 5 explained in Embodiment 1; the second X-direction scanning electromagnet power source 635 and the X-direction scanning electromagnet 620 perform operation corresponding to the operation of the second scanning electromagnet power source 63 and the X-direction scanning electromagnet 62 of the second scanning electromagnet 6 explained in Embodiment 1. Similarly, the first Y-direction scanning electromagnet power source 536 and the Y-direction scanning electromagnet 610 perform operation corresponding to the operation of the first scanning electromagnet power source 53 and the Y-direction scanning electromagnet 51 of the first scanning electromagnet 5 explained in Embodiment 1; the second 1-direction scanning electromagnet power source 636 and the 1-direction scanning electromagnet 610 perform operation corresponding to the operation of the second scanning electromagnet power source 63 and the Y-direction scanning electromagnet 61 of the second scanning electromagnet 6 explained in Embodiment 1. In other words, as explained in Embodiment 1, from the high-frequency components separated by the frequency separation unit 71 from a desired orbit signal, the command value conversion unit 72 obtains command values for the first X-direction scanning electromagnet power source 535 and the first Y-direction scanning electromagnet power source 536. Similarly, from the low-frequency components separated by the frequency separation unit 71 from the desired orbit signal, the command value conversion unit 72 obtains command values for the second X-direction scanning electromagnet power source 635 and the second Y-direction scanning electromagnet power source 636.

As described above, the particle beam irradiation apparatus according to Embodiment 6 makes it possible to generate respective command values for two scanning electromagnet power sources, whose response speeds are different from each other, for each one of X-direction and Y-direction scanning electromagnets, with a simple configuration of only frequency-separating a desired orbit signal; thus, scanning of a charged particle beam can be performed with a high flexibility in the speed, from a low speed to a high speed. Moreover, in the case where the foregoing particle beam irradiation apparatus is applied to a particle beam therapy system, an appropriate desired orbit for each patient can be formed, and scanning can be performed, taking into consideration the characteristics of the scanning electromagnets in each pair; therefore, the scanning time can be reduced.

The same technical idea as explained in Embodiment 2 may be applied to Embodiment 6. In other words, the configuration may be in such a way that for each one of X-direction and Y-direction scanning electromagnets, there are provided three power sources, i.e., high-speed, middle-speed, and low-speed power sources, or four or more power sources whose response speeds are different from one another. In addition, it goes without saying that with regard to the command value creation method or the like, not only Embodiment 1 but also Embodiments 3 through 5 can be applied to Embodiment 6.

Embodiment 7

Figure 22:
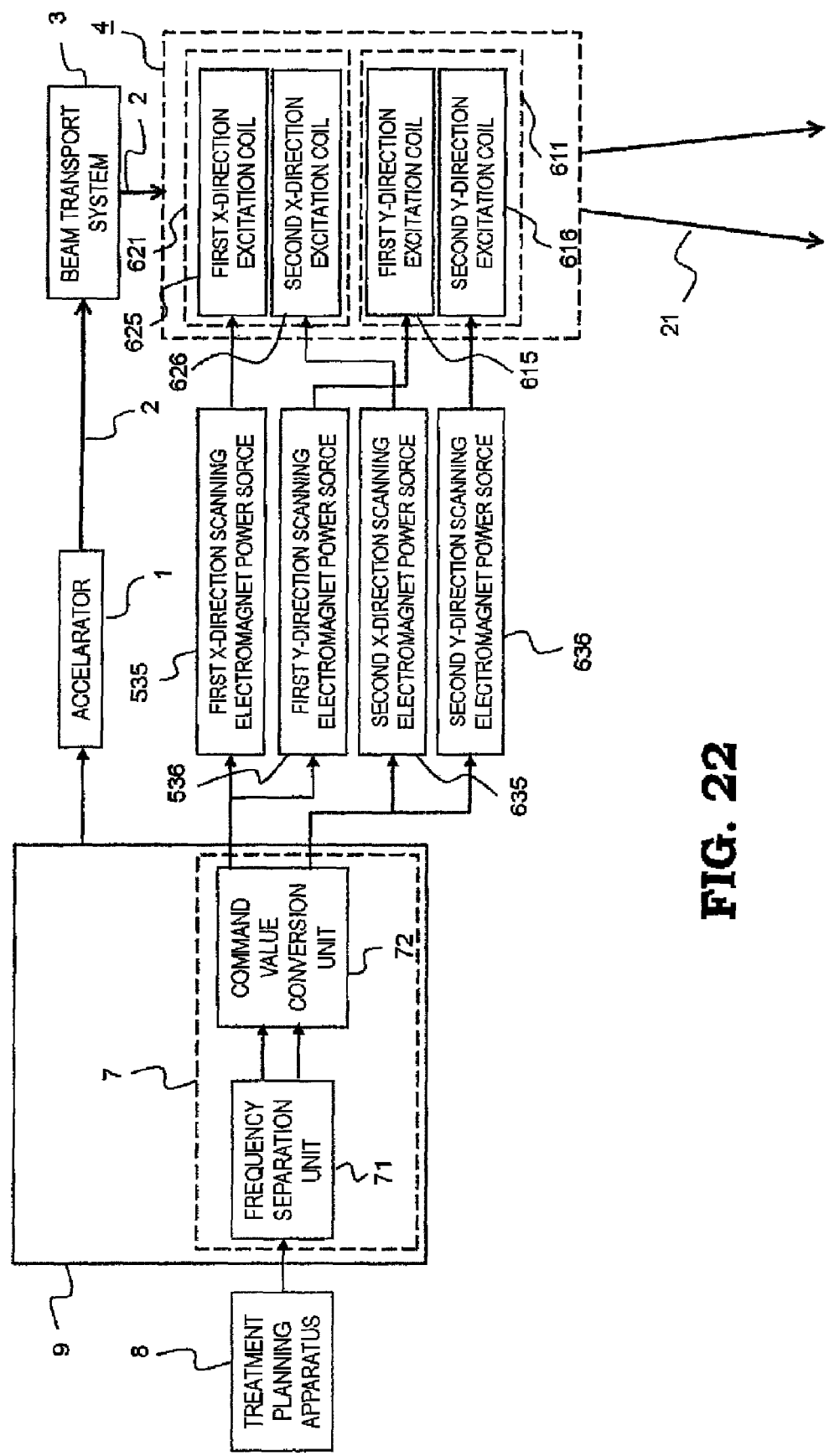
FIG. 22 is a block diagram schematically illustrating the configuration of a particle beam therapy system including a particle beam irradiation apparatus according to Embodiment 7 of the present invention.

FIG. 22 is a block diagram illustrating the configuration of a particle beam irradiation apparatus according to Embodiment of the present invention. In FIG. 22, the same reference numerals as those in FIGS. 1 and 21 denote the same or equivalent elements or components. In Embodiment 7, as the scanning electromagnet that deflects the particle beam 2 in the X direction so as to perform scanning, only an X-direction scanning electromagnet 621 is provided. In this regard, however, the X-direction scanning electromagnet 621 is formed in such a way that two excitation coils, i.e., a first X-direction excitation coil 625 and a second X-direction excitation coil 626 are wound around a single and the same iron core. The number of coil turns of the second X-direction excitation coil 626 is larger than that of the first X-direction excitation coil 625; thus, the second X-direction excitation coil 626 has a large inductance, and the first X-direction excitation coil 625 has a small inductance. The first X-direction excitation coil 625 is driven by the first X-direction scanning electromagnet power source 535 having a fast response speed; the second X-direction excitation coil 626 is driven by the second X-direction scanning electromagnet power source 635 having a response speed that is lower than that of the first X-direction scanning electromagnet power source 535.

The range of scanning that can be performed in such a way that the first X-direction excitation coil 625 driven by the first X-direction scanning electromagnet power source 535 energizes the X-direction scanning electromagnet 621 so that the particle beam 2 is deflected is the same as the range of scanning that can be performed by the X-direction scanning electromagnet 52 of the first scanning electromagnet 5 in Embodiment 1. The range of scanning that can be performed in such a way that the second X-direction excitation coil 626 driven by the second X-direction scanning electromagnet power source 635 energizes the X-direction scanning electromagnet 621 so that the particle beam 2 is deflected is the same as the range of scanning that can be performed by the X-direction scanning electromagnet 62 of the second scanning electromagnet 6 in Embodiment 1. That is to say, the particle beam 2 can be largely deflected and scanned with the second X-direction excitation coil 626 driven by the second X-direction scanning electromagnet power source 635, but cannot be scanned at high speed. With the first X-direction excitation coil 625 driven by the first X-direction scanning electromagnet power source 535, the particle beam 2 can be scanned at high speed, but cannot be largely scanned.

Similarly, the Y-direction scanning electromagnet 611 is formed in such a way that two excitation coils, i.e., a first Y-direction excitation coil 615 and a second Y-direction excitation coil 616 are wound around a single and the same iron core. The number of coil turns of the second Y-direction excitation coil 616 is larger than that of the first Y-direction excitation coil 615; thus, the second Y-direction excitation coil 616 has a large inductance, and the first Y-direction excitation coil 615 has a small inductance. The first Y-direction excitation coil 615 is driven by the first Y-direction scanning electromagnet power source 536 having a fast response speed; the second Y-direction excitation coil 616 is driven by the second Y-direction scanning electromagnet power source 636 having a response speed that is lower than that of the first Y-direction scanning electromagnet power source 536.

The range of scanning that can be performed in such a way that the first Y-direction excitation coil 615 driven by the first YX-direction scanning electromagnet power source 536 energizes the Y-direction scanning electromagnet 611 so that the particle beam 2 is deflected is the same as the range of scanning that can be performed by the Y-direction scanning electromagnet 51 of the first scanning electromagnet 5 in Embodiment 1. The range of scanning that can be performed in such a way that the second Y-direction excitation coil 616 driven by the second Y-direction scanning electromagnet power source 636 energizes the Y-direction scanning electromagnet 611 so that the particle beam 2 is deflected is the same as the range of scanning that can be performed by the Y-direction scanning electromagnet 61 of the second scanning electromagnet 6 in Embodiment 1. That is to say, the particle beam 2 can be largely deflected and scanned with the second Y-direction excitation coil 616 driven by the second Y-direction scanning electromagnet power source 636, but cannot scanned at high speed. With the first Y-direction excitation coil 615 driven by the first Y-direction scanning electromagnet power source 536, the particle beam 2 can be scanned at high speed, but cannot be largely scanned.

In the particle beam irradiation apparatus according to Embodiment 7, the first X-direction scanning electromagnet power source 535 and the first X-direction excitation coil 625 of the X-direction scanning electromagnet 621 perform operation corresponding to the operation of the first scanning electromagnet power source 53 and the X-direction scanning electromagnet 52 of the first scanning electromagnet 5 explained in Embodiment 1; the second X-direction scanning electromagnet power source 635 and the second X-direction excitation coil 626 of the X-direction scanning electromagnet 621 perform operation corresponding to the operation of the second scanning electromagnet power source 63 and the X-direction scanning electromagnet 62 of the second scanning electromagnet 6 explained in Embodiment 1. Similarly, the first Y-direction scanning electromagnet power source 536 and the first Y-direction excitation coil 615 of the Y-direction scanning electromagnet 611 perform operation corresponding to the operation of the first scanning electromagnet power source 53 and the Y-direction scanning electromagnet 51 of the first scanning electromagnet 5 explained in Embodiment 1; the second Y-direction scanning electromagnet power source 636 and the second Y-direction excitation coil 616 of the Y-direction scanning electromagnet 611 perform operation corresponding to the operation of the second scanning electromagnet power source 63 and the Y-direction scanning electromagnet 61 of the second scanning electromagnet 6 explained in Embodiment 1. In other words, as explained in Embodiment 1, from the high-frequency components separated by the frequency separation unit 71 from a desired orbit signal, the command value conversion unit 72 obtains command values for the first X-direction scanning electromagnet power source 535 and the first Y-direction scanning electromagnet power source 536. Similarly, from the low-frequency components separated by the frequency separation unit 71 from the desired orbit signal, the command value conversion unit 72 obtains command values for the second X-direction scanning electromagnet power source 635 and the second Y-direction scanning electromagnet power source 636.

As described above, in the particle beam irradiation apparatus according to Embodiment 7, two excitation coils, the respective inductances of which are small and large, are wound around each one of the X-direction and Y-direction scanning electromagnets, so that it is made possible to generate command values for the respective scanning electromagnet power sources, with a simple configuration only to frequency-separate a desired orbit signal; thus, scanning of a charged particle beam can be performed with a high flexibility in the speed, from a low speed to a high speed. Moreover, in the case where the foregoing particle beam irradiation apparatus is applied to a particle beam therapy system, an appropriate desired orbit for each patient can be formed, and scanning can be performed, taking into consideration the respective characteristics of the scanning electromagnet power sources and the excitation coils; therefore, the scanning time can be reduced.

The same technical idea as explained in Embodiment 2 may be applied to Embodiment 7. In other words, the configuration may be in such a way that for each one of X-direction and Y-direction scanning electromagnets, there are provided three excitation coils, i.e., small-inductance, middle-inductance, and large-inductance excitation coils, or four or more excitation coils whose inductances are different from one another. In addition, it goes without saying that with regard to the command value creation method or the like, not only Embodiment 1 but also Embodiments 3 through 5 can be applied to Embodiment 7.

DESCRIPTION OF REFERENCE NUMERALS

1: accelerator
2: charged particle beam
3: beam transport system
4: beam irradiation system
5: 1st scanning electromagnet
6: 2nd scanning electromagnet
7: cooperative control scanning control unit
8, 80: treatment planning apparatus
20: beam axis
21: scanned charged particle beam
22: irradiation subject
23: scanning area of whole beam irradiation system
24: scanning area (default) of 1st scanning electromagnet
51, 61, 610, 611: Y-direction scanning electromagnet
52, 62, 620, 621: X-direction scanning electromagnet
535: 1st X-direction scanning electromagnet power source
536: 1st Y-direction scanning electromagnet power source
615: 1st Y-direction excitation coil
616: 2nd Y-direction excitation coil
625: 1st X-direction excitation coil
616: 2nd X-direction excitation coil
635: 1st X-direction scanning electromagnet power source
636: 1st Y-direction scanning electromagnet power source
71: frequency separation unit
72: command value conversion unit
73: lowpass filter
74: high-pass filter
O: isocenter

The invention claimed is:

1. A particle beam irradiation apparatus that scans a charged particle beam on two directions of X-direction and Y-direction desired orbits perpendicular to a travelling direction of the charged particle beam and irradiates the charged particle beam onto an irradiation subject comprising;
two or more pairs of scanning electromagnets that scan the charged particle beam in the two directions,
wherein the desired orbit is given by time-series desired orbit data in which desired irradiation positions corresponding to time are specified;
and command values for respective scanning electromagnets in the two or more pairs of scanning electromagnets are generated based on plural pieces of data obtained by frequency-separating the time-series desired orbit data.

2. The particle beam irradiation apparatus according to claim 1, wherein electric frequency response characteristics of the scanning electromagnets in different pairs are different from one another.

3. The particle beam irradiation apparatus according to claim 2, wherein two pairs of scanning electromagnets exist.

4. The particle beam irradiation apparatus according to claim 3, wherein the pair of scanning electromagnets that are arranged at an upstream side of the charged particle beam has higher frequency response characteristics than the pair of scanning electromagnets that are arranged at a downstream side thereof.

5. The particle beam irradiation apparatus according to claim 1, wherein command values for respective scanning electromagnets in the two or more pairs of scanning electromagnets are generated with inverse-map formula models, based on plural pieces of data obtained by frequency-separating the time-series desired orbit data.

6. A particle beam irradiation apparatus that scans an incident charged particle beam on two directions of X-direction and Y-direction desired orbits perpendicular to a travelling direction of the charged particle beam and irradiates the charged particle beam onto an irradiation subject comprising;
an X-direction scanning electromagnet that scans the charged particle beam in the X direction;
a plurality of X-direction scanning electromagnet power sources that energize the X-direction scanning electromagnet and whose response speeds are different from one another;
a Y-direction scanning electromagnet that scans the charged particle beam in the Y direction; and
a plurality of Y-direction scanning electromagnet power sources that energize the Y-direction scanning electromagnet and whose response speeds are different from one another,
wherein the desired orbit is given by time-series desired orbit data in which desired irradiation positions corresponding to time are specified;
and command values for the plurality of X-direction scanning electromagnet power sources and the plurality of Y-direction scanning electromagnet power sources are generated based on plural pieces of data obtained by frequency-separating the time-series desired orbit data.

7. The particle beam irradiation apparatus according to claim 6, wherein currents from the plurality of X-direction scanning electromagnet power sources are superimposed on one another and flow in a single excitation coil for energizing the X-direction scanning electromagnet, and currents from the plurality of Y-direction scanning electromagnet power sources are superimposed on one another and flow in a single excitation coil for energizing the Y-direction scanning electromagnet.

8. The particle beam irradiation apparatus according to claim 6, further including:
a plurality of X-direction excitation coils that energize the X-direction scanning electromagnet and whose inductances are different from one another; and
a plurality of Y-direction excitation coils that energize the Y-direction scanning electromagnet and whose inductances are different from one another,
wherein each one of the plurality of X-direction scanning electromagnet power sources supplies a current to the corresponding one of the plurality of X-direction excitation coils; and each one of the plurality of Y-direction scanning electromagnet power sources supplies a current to the corresponding one of the plurality of Y-direction excitation coils.

9. A particle beam therapy system including the particle beam irradiation apparatus according to claim 1 and a treatment planning apparatus that generates the desired orbit.

10. A particle beam therapy system including the particle beam irradiation apparatus according to claim 6 and a treatment planning apparatus that generates the desired orbit.

* * * * *